United States Patent

Strickland

[11] Patent Number: 5,856,298
[45] Date of Patent: Jan. 5, 1999

[54] ERYTHROPOIETIN ISOFORMS

[75] Inventor: Thomas Wayne Strickland, Moorpark, Calif.

[73] Assignee: Amgen Inc., Thousand Oaks, Calif.

[21] Appl. No.: 334,882

[22] Filed: Nov. 3, 1994

Related U.S. Application Data

[63] Continuation of Ser. No. 942,126, Sep. 8, 1992, abandoned, which is a continuation of Ser. No. 594,448, Oct. 12, 1990, abandoned, which is a continuation-in-part of Ser. No. 421,444, Oct. 13, 1989, abandoned.

[51] Int. Cl.$^6$ .................. A61K 38/18; C07K 14/505; C07K 1/18; C07K 1/28
[52] U.S. Cl. .................. 514/8; 530/395; 530/397; 530/412; 530/416; 435/69.4; 204/182.9
[58] Field of Search .................. 530/395, 397, 530/416, 412; 514/8; 435/69.4; 204/182.9

[56] References Cited

U.S. PATENT DOCUMENTS

| | | | |
|---|---|---|---|
| 4,377,513 | 3/1983 | Sugimoto et al. | 530/395 |
| 4,667,016 | 5/1987 | Lai et al. | 435/69.6 |
| 4,703,008 | 10/1987 | Lin | 435/240.2 |
| 4,801,540 | 1/1989 | Hiatt et al. | 435/172.3 |
| 4,888,282 | 12/1989 | Beremand et al. | 435/172.3 |
| 5,002,870 | 3/1991 | Leavitt et al. | 530/350 |
| 5,451,662 | 9/1995 | Naveh et al. | 530/416 |

FOREIGN PATENT DOCUMENTS

| | | |
|---|---|---|
| 267 678 | 5/1988 | European Pat. Off. . |
| 0409113 | 1/1991 | European Pat. Off. . |

OTHER PUBLICATIONS

Fuhr et al., *Biochemical and Biophysical Research Communications* 98: 930–935, Feb. 27,1981.
Viau et al., *Biochemical and Biophysical Research Communications* 117: 324–331, Nov. 30, 1983.
Havel et al., *Proc. Natl. Acad. Sci.* 77: 4349–4353, Jul. 1980.
Welch et al., *Journal of Biological Chemistry* 259: 4501–4513, Apr. 1984.
Napier et al "Isoelectric Focussing of Human Urinary Erythropoietiu" *IRCS Med. SCI*4:437 (1976).
Andreux et al "Étude de l'érythropoiétiue. . . " *Annales Pharma. Francaises* 31(1):29–36, (1973).
Fuhr et al., *Biochem. & Biophys. Res. Comm.*98: 930–935, Feb. 27, 1981.
Viau et al., *Biochem. & Biophys. Res. Comm.* 117: 324–331, Nov/ 30, 1983.
Havel et al., *PNAS* 77: 4349–4353, Jul. 1980.
Krystal et al., *Blood* 67: 71–79, Jan. 1986.
Welch et al., *J. Biol. Chem.* 259: 4501–4513, Apr. 1984.
Dordal et al., *Endocrinology* 116: 2293–2299, 1985.
Sasaki et al., *J. Biol. Chem.* 262:12059–12076, Sep. 5, 1987.
Copsey et al., *Genetically Eng. Human Therap. Drugs*, pp. 25–26, 257, 1988.
Dube et al., *J. Biol. Chem.* 263:17516–17521, 25 Nov. 1988.
Goldwasser, "Erythropoietiu & red cell differentiation", in *Control of Cellular Division and Devel: Part A*, pp. 487–494, 1981.
Lukowsky et al, "Studies on the role of Sialic Acid in The hysical and Biological Properties of Erythropoietin", *Can. J. Biochem.* 50:909–917, 1972.
Ashwell et al. Methods Enzymol. 50 , 287–288 (1978).
Bradford Anal. Biochem. 72 , 248–254 (1976).
Burnette et al. Anal. Biochem. 112 , 195–203 (1981).
Cotes et al. Nature 191 , 1065–1067 (Sep. 1961).
Davis et al. Biochemistry 26 , 2633–2638 (1987).

(List continued on next page.)

*Primary Examiner*—Stephen G. Walsh
*Attorney, Agent, or Firm*—Robert B. Winter; Steven M. Odre; Ron K. Levy

[57] ABSTRACT

Erythropoietin isoforms having a specific number of sialic acids per erythropoietin molecule are disclosed. Also disclosed are mixtures of such isoforms, pharmaceutical compositions containing such isoforms or mixtures thereof and methods of obtaining the erythropoietin isoforms.

31 Claims, 13 Drawing Sheets in vivo U per mG Erythropoietin Polypeptide (Calculated from Radioimmunoassay)

OTHER PUBLICATIONS

Egrie et al. Immunobiology 1721, 213–224 (1986).
Elliott et al. Blood 74, Supp. 1, A 1228 (1989).
Elliott et al. Gene 79, 167–180 (1989).
Fukuda et al. Blood 73, 84–89 (Jan. 1989).
Goldwasser et al. J. Biol. Chem. 249, 4202–4206 (Jul. 1974).
Holmes et al. Anal. Biochem. 117, 193 (1981).
Iscove et al. J.Cell Physiol. 83, 309–320 (1974).
Kunkel et al. Methods Enzymol. 154, 367–382 (1987).
Lai et al. J. Biol. Chem. 261, 3116–3121 (Mar. 1986).
Law et al. Proc. Natl. Acad. Sci. USA 83, 6920–6924 (Sep. 1986).
Lee et al. J. Biol. Chem. 264, 13848–13855 (Aug. 1989).
Lin et al. Proc. Natl. Acad. Sci. USA 82, 7580–7584 (Nov. 1985).
Messing Methods Enzymol. 101, 20–78 (1983).
Miyake et al. J. Biol. Chem., 252, 5558–5564 (Aug. 1977).
Morrell et al. J. Biol Chem 243, 155–59 (Jan. 1968).
Mutsaers et al. Eur. J. Biochem. 156, 651–654 (1986).
Phelps et al. Biochem. Biophys. Acta. 791, 226–238 (1984).
Shelton et al Biochem. Med. 12, 45–54 (1975).
Takeuchi et al. J. Biol. Chem. 263, 3657–3663 (Mar. 1988).
Takeuchi et al. J. Chromatogr. 400, 207–213 (1987).
Yanisch–Perron et al. Gene 33, 103–119 (1985).
Dorado et al. Biochem. Medicine 6, 238–245 (1972).
Napier IRCS Med. Sci. Biochem. 4, 437 (1976).

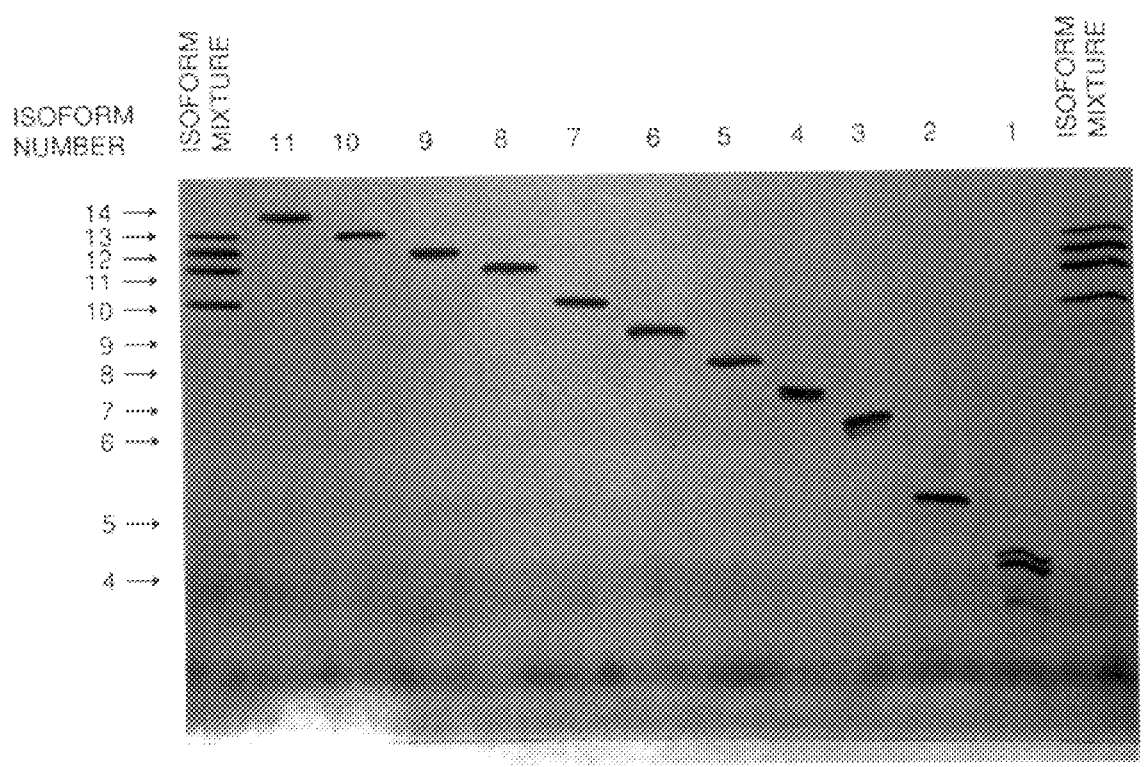

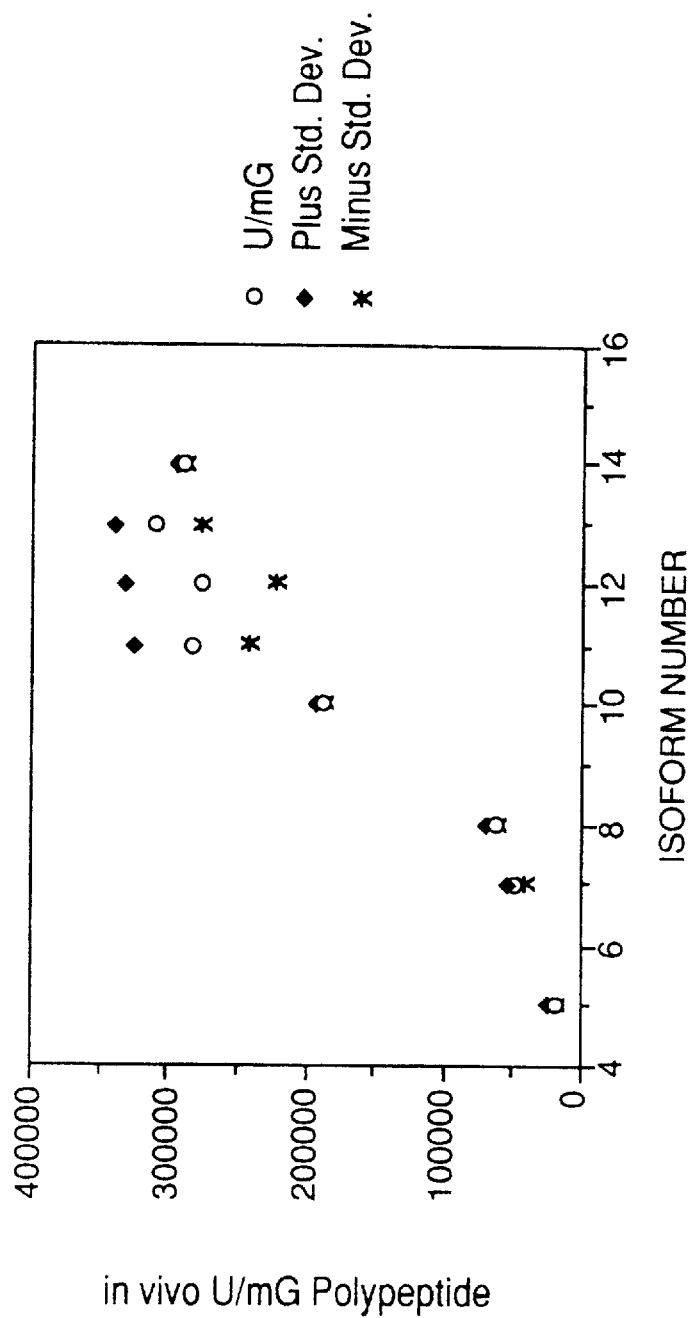

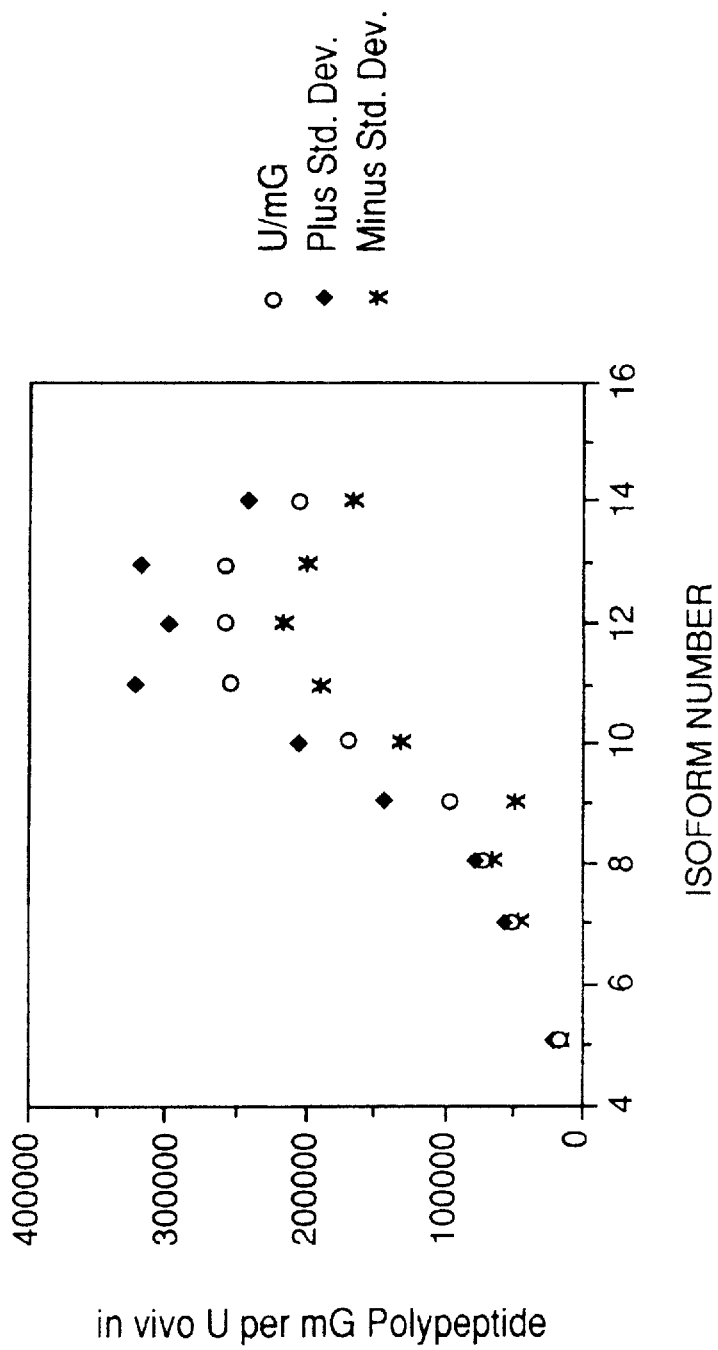

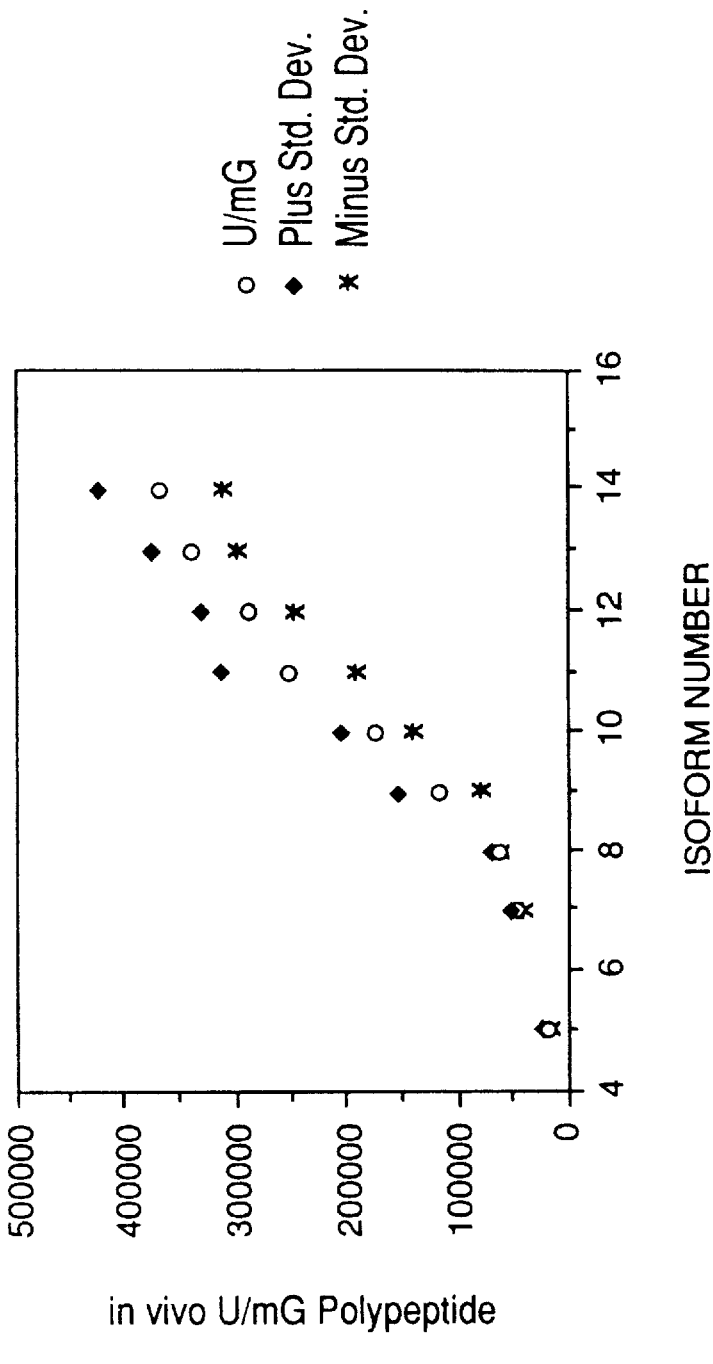

FIG. 5

```
 -27                              +1        10        20    □
MGVHECPAWLWLLLSLLSLPLGLPVLGAPPRLICDSRVLERYLLEAKEAENIT
                                 ↓↓        ↓↓
                                 N S       N S
                                 □         □

30      □40       50        60        70
  TGCAEHCSLNENITVPDTKVNFYAWKRMEVGQQAVEVWQGLALLSEAVLRGQA
                                           ↓
                                           N
                                           □

*
                                                    T
                                                    ↑
 80   □     90       100      110       120    ↑ *  130
  LLVNSSQPWEPLQLHVDKAVSGLRSLTTLLRALGAQKEAISPPDAASAAPLRT
                                           ↓↓ ↓
                                           NN S
                                           □□
```

140       150       160           □ = Site for N-glycosylation
  ITADTFRKLFRVYSNFLRGKLKLYTGEACRTGDR
                  ↓ ↓                  * = Site for O-glycosylation
                  N S
                  □

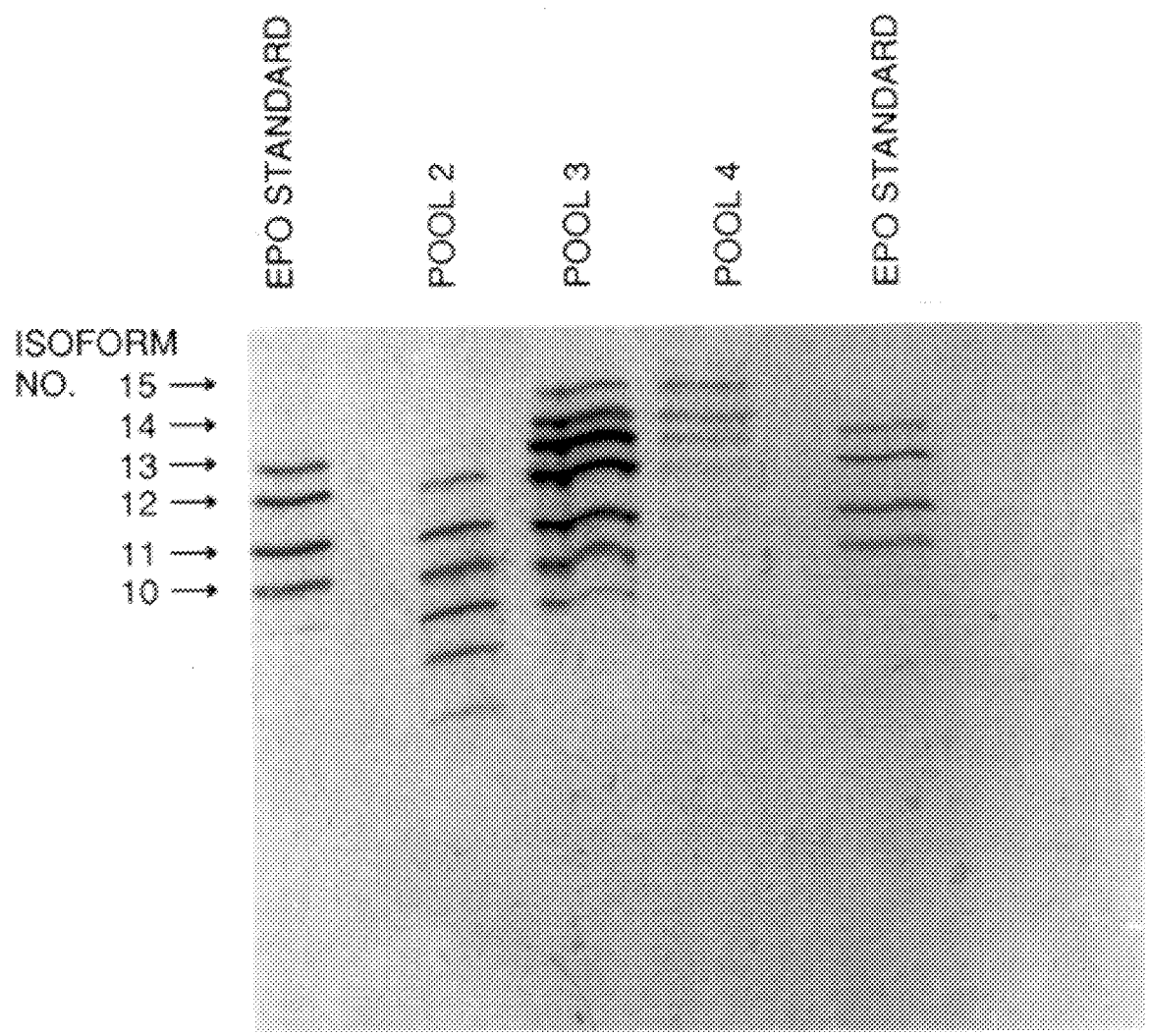

ERYTHROPOIETIN ISOFORMS

This application is a continuation, of application Ser. No. 07/942,126, filed Sep. 8, 1992, now abandoned, which is hereby incorporated by reference, which is a continuation of application Ser. No. 07/594,448 filed on Oct. 12, 1990, now abandoned, which is a continuation-in-part application of U.S. application Ser. No. 421,444, filed Oct. 13, 1989, now abandoned, which is incorporated by reference. The present invention relates to erythropoietin isoforms or mixtures thereof, to the methods for the preparation of specific isoforms or mixtures thereof, to pharmaceutical compositions comprising such isoforms or mixtures thereof, and to methods of treatment utilizing such isoforms and compositions.

BACKGROUND OF THE INVENTION

Erythropoietin is a glycoprotein hormone involved in the maturation of erythroid progenitor cells into erythrocytes. It is essential in regulating levels of red blood cells in circulation. Naturally occurring erythropoietin is produced by the liver during fetal life and by the kidney of adults and circulates in the blood and stimulates the production of red blood cells in bone marrow. Anemia is almost invariably a consequence of renal failure due to decreased production of erythropoietin from the kidney. Recombinant erythropoietin produced by genetic engineering techniques involving the expression of a protein product from a host cell transformed with the gene encoding erythropoietin has been found to be effective when used in the treatment of anemia resulting from chronic renal failure.

Until recently, the availability of erythropoietin has been very limited. Although the protein is present in human urine, excreted levels are too low to make this a practical source of erythropoietin for therapeutic use. Patients suffering from aplastic anemia exhibit elevated levels of urinary erythropoietin relative to healthy individuals, but limited supplies of this urine also make such a source impractical. The purification of human urinary erythropoietin by Miyake et al. in J. Biol. Chem., 252, 5558 (1977), used, as starting material, urine from aplastic anemic individuals.

The identification, cloning, and expression of genes encoding erythropoietin are described in U.S. Pat. No. 4,703,008 to Lin. A description of the purification of recombinant erythropoietin from cell medium that supported the growth of mammalian cells containing recombinant erythropoietin plasmids for example, is included in U.S. Pat. No. 4,667,016 to Lai et al. The expression and recovery of biologically active recombinant erythropoietin from mammalian cell hosts containing the erythropoietin gene on recombinant plasmids has, for the first time, made available quantities of erythropoietin suitable for therapeutic applications. In addition, knowledge of the gene sequence and the availability of larger quantities of purified protein has led to a better understanding of the mode of action of this protein.

The biological activity of a protein is dependent upon its structure. In particular, the primary structure of a protein (i.e., its amino acid sequence) provides information that allows the formation of secondary (e.g, α helix or β-sheet) and tertiary (overall three-dimensional folding) structures by a polypeptide during and after its synthesis. The disruption of proper secondary and tertiary structures by the introduction of mutations or by chemical or enzymatic treatments can result in a reduction in biological activity.

In procaryotic organisms, the biological activities of proteins are largely governed by the structures described above.

Unlike proteins from procaryotic cells, many cell surface and secretory proteins produced by eucaryotic cells are modified with one or more oligosaccharide groups. This modification, referred to as glycosylation, can dramatically affect the physical properties of proteins and can also be important in protein stability, secretion, and subcellular localization. Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Glycosylation occurs at specific locations along the polypeptide backbone and is usually of two types: O-linked oligosaccharides are attached to serine or threonine residues while N-linked oligosaccharides are attached to asparagine residues when they are part of the sequence Asn-X-Ser/Thr, where X can be any amino acid except proline. The structures of N-linked and O-linked oligosaccharides and the sugar residues found in each type are different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein.

Both human urinary derived erythropoietin and recombinant erythropoietin (expressed in mammalian cells) having the amino acid sequence 1-165 of human erythropoietin contain three N-linked and one O-linked oligosaccharide chains which together comprise about 40% of the total molecular weight of the glycoprotein. N-linked glycosylation occurs at asparagine residues located at positions 24, 38 and 83 while O-linked glycosylation occurs at a serine residue located at position 126 (Lai et al. J. Biol. Chem. 261, 3116 (1986); Broudy et al. Arch. Biochem. Biophys. 265, 329 (1988)). The oligosaccharide chains have been shown to be modified with terminal sialic acid residues. Enzymatic treatment of glycosylated erythropoietin to remove all sialic acid residues results in a loss of in vivo activity but does not affect in vitro activity (Lowy et al. Nature 185, 102 (1960); Goldwasser et al. J. Biol. Chem. 249, 4202 (1974)). This behavior has been explained by rapid clearance of asialoerythropoietin from circulation upon interaction with the hepatic asialoglycoprotein binding protein (Morrell et al. J. Biol. Chem. 243, 155 (1968); Briggs, et al. Am. J. Physiol. 227, 1385 (1974); Ashwell et al. Methods Enzymol. 50, 287 (1978)). Thus, erythropoietin possesses in vivo biological activity only when it is sialylated to avoid its binding by the hepatic binding protein.

The role of the other components in the oligosaccharide chains of erythropoietin is not well defined. It has been shown that non-glycosylated erythropoietin has greatly reduced in vivo activity compared to the glycosylated form but does retain in vitro activity (Dordal et al. Endocrinology 116, 2293 (1985); Lin patent, supra). In another study, however, the removal of N-linked or O-linked oligosaccharide chains singly or together by mutagenesis of asparagine or serine residues that are glycosylation sites sharply reduces in vitro activity of the altered erythropoietin that is produced in mammalian cells (Dube et al. J. Biol. Chem. 263, 17516 (1988)).

Glycoproteins such as erythropoietin can be separated into different charged forms using techniques such as isoelectric focusing (IEF). Several parties have reported IEF studies of crude and partially purified erythropoietin preparations (Lukowsky et al., J. Biochem 50, 909 (1972); Shelton et al. Biochem. Med. 12, 45 (1975); Fuhr et al. Biochem.

Biophys. Res. Comm. 98, 930 (1981)). At most, three or four fractions having erythropoietin activity were distinguished by IEF in these studies and none were characterized with respect to carbohydrate content. In addition, no correlation between the isoelectric points of the fractions and their biological activity was made.

During the purification of urinary erythropoietin from human urine discussed in Miyake et. al. supra, two erythropoietin fractions from hydroxylapatite chromatography designated II and IIIA were reported to have the same specific activity. A subsequent carbohydrate analysis of fractions II and IIIA revealed that fraction II had a greater average sialic acid content than fraction IIIA (Dordal et. al. supra).

It is an object of the present invention to provide separated and isolated isoforms of erythropoietin having a defined sialic acid content and biological activity. Pharmaceutical compositions containing such molecules would have therapeutic benefit.

SUMMARY OF THE INVENTION

The subject invention relates to erythropoietin isoforms. Also provided is a method of preparing an erythropoietin isoform comprising the steps of subjecting purified erythropoietin to preparative isoelectric focusing, and eluting a single isoform from the gel. Pharmaceutically acceptable compositions comprising erythropoietin isoforms are also provided. This invention also relates to methods of increasing hematocrit levels in mammals comprising administering a therapeutically acceptable amount of these compositions to increase production of reticulocytes and red blood cells.

The subject invention relates to a method of preparing a mixture of erythropoietin molecules having greater than or alternatively less than a predetermined number of sialic acids per molecule comprising subjecting material containing erythropoietin to ion exchange chromatography. Also comprised by the subject invention is a method of preparing a mixture of erythropoietin molecules having greater than or alternatively less than a predetermined number of sialic acids per molecule comprising subjecting a material containing erythropoietin to chromatofocusing.

The invention also comprises analogs of human erythropoietin having a greater number of sites for carbohydrate chain attachment than human erythropoietin, such as [$Asn^{69}$] EPO; [$Asn^{125}$, $Ser^{127}$] EPO; [$Thr^{125}$] EPO; and [$Pro^{124}$, $Thr^{125}$] EPO.

BRIEF DESCRIPTION OF THE DRAWINGS

FIG. 1 shows an analytical isoelectric focusing gel of the separate recombinant erythropoietin isoforms. Gel lanes 1–11 show isoforms ranging from less acidic (higher pI) in lane 1 to more acidic (lower pI), in lane 11. Purified recombinant erythropoietin containing a mixture of isoforms 9–14 is also shown in the far left and right lanes of the gel.

FIG. 2A, FIG. 2B and FIG. 2C show the relationship between the number of sialic acids per erythropoietin isoform and the in vivo specific activity of each isoform expressed as units per mg of erythropoietin polypeptide. In FIG. 2A, the concentration of each erythropoietin isoform was determined by the Bradford protein assay; in 2B, the concentration was determined by absorbance at 280 nm, in 2C, the concentration was determined by RIA.

FIG. 5 shows the amino acid sequence of human erythropoietin. Squares indicate asparagine residues to which carbohydrate chains are attached and asterisks indicate threonine and serine residues modified with carbohydrate. Additional glycosylation sites provided in the analogs of Example 6 are indicated by mutations to asparagine serine, and threonine.

FIG. 9 shows an isoelectric focusing gel of pools 2, 3 and 4 obtained by Q-Sepharose and C4 reverse phase chromatography of cell medium that supported the growth of CHO cells transfected with erythropoietin cDNA containing the [$Thr^{125}$] mutation. Purified recombinant erythropoietin containing a mixture of isoforms are obtained using procedures described in Example 2 of Lai et al., supra, except that DEAE-Agarose chromatography is replaced by Q-Sepharose chromatography, is also shown in the left and right lanes of the gel.

DETAILED DESCRIPTION OF THE INVENTION

Figure 3:
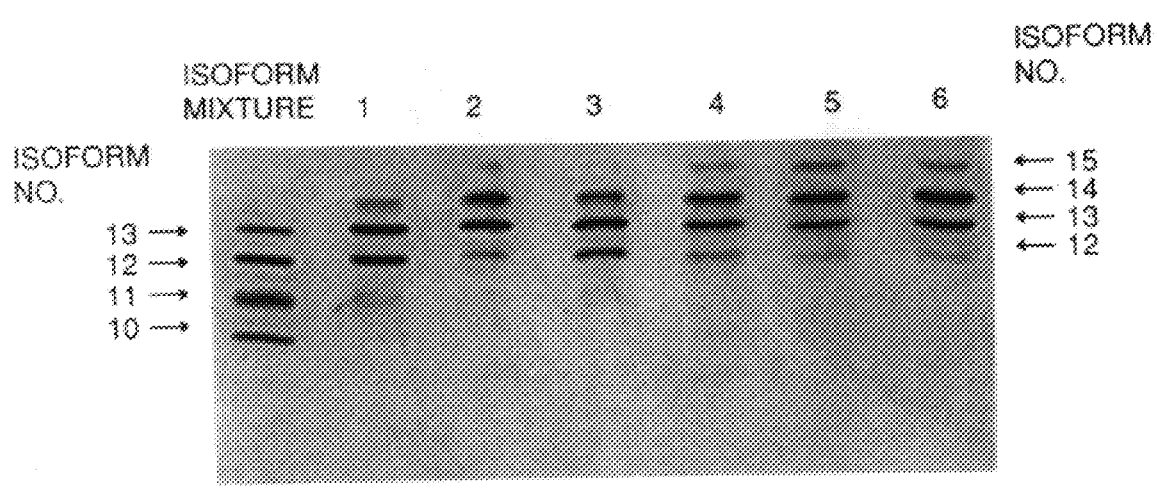
FIG. 3 shows an analytical isoelectric focusing gel of defined mixtures of recombinant erythropoietin isoforms prepared by anion exchange chromatography under different conditions. Gel lanes 1–6 represent, respectively, erythropoietin isoforms eluted in a high salt wash after washing the Q-Sepharose fast flow column with 150 mM acetic acid, pH 4.7, 150 mM acetic acid (unbuffered), 200 mM acetic acid, pH 4.7, 250 mM acetic acid, pH 4.7, 300 mM acetic acid, pH 4.7 or 300 mM acetic acid (unbuffered). Purified recombinant erythropoietin containing a mixture of isoforms as obtained using procedures described in Example 2 of Lai et al., supra, except that DEAE-Agarose chromatography is replaced by Q-Sepharose chromatography, is also shown in the far left lane of the gel.

According to the present invention, erythropoietin isoforms are provided. Isoelectric focusing (IEF) separates proteins on the basis of charge. When placed in a pH gradient and subjected to an electric field, proteins will migrate to the point at which they have no net charge and remain there. This is the isoelectric point (pI) of the protein. Each distinct band observed on IEF represents molecules that have a particular pI and therefore the same overall charge, and is termed an isoform. The term "erythropoietin isoform" as used herein refers to erythropoietin preparations having a single pI, and having the same amino acid sequence.

In a preferred embodiment the erythropoietin is the product of the expression of an exogenous DNA sequence that has been transfected into a non-human eucaryotic host cell, that is, in a preferred embodiment the erythropoietin is "recombinant erythropoietin". Recombinant erythropoietin is advantageously produced according to the procedures described in commonly owned Lin U.S. Pat. No. 4,703,008 hereby incorporated by reference. Recombinant erythropoietin is advantageously purified according to the general procedures described in Example 2 of commonly owned Lai et al. U.S. Pat. No. 4,667,016 hereby incorporated by reference, or alternatively the procedure described in Example 2 wherein DEAE-Agarose chromatography is replaced by Q-Sepharose chromatography. In the Q-Sepharose column modification, 55 mM NaCl replaces 25 mM NaCl in the buffer solution used to bring the column to neutral pH, and 140 mM NaCl replaces 75 mM NaCl in the buffer solution used to elute erythropoietin from the column. This material, when analyzed by sodium dodecyl sulfate polyacrylamide gel electrophoresis, migrates as a single species (i.e. band). When purified erythropoietin is subjected to IEF, multiple bands in the gel are apparent, indicating that different charged forms of the glycoprotein are present.

It has been found that discrete isoforms of recombinant erythropoietin having the amino acid sequence of urinary derived human erythropoietin correspond to erythropoietin molecules having from 1–14 sialic acids, and each isoform present in purified recombinant erythropoietin has an in vivo activity which is related to the number of sialic acids the isoform possesses. The term "erythropoietin", as used herein, includes naturally occurring erythropoietin, urinary derived human erythropoietin as well as non-naturally occurring polypeptides having an amino acid sequence and glycosylation sufficiently duplicative of that of naturally occurring erythropoietin to allow possession of in vivo biological properties of causing bone marrow cells to increase production of reticulocytes and red blood cells.

Crude preparations of erythropoietin have many isoforms but material purified for example, as in the Lai et al. patent supra Example 2, contains predominantly six isoforms when analyzed by IEF. In addition, at least one additional isoform of greater acidity has been detected using the chromatographic procedures described in Example 4. (This more acidic form, migrating at >14 sialic acids on an IEF gel may contain nonsialic acid negative charges as shown by the resistance of some of the charge to sialidase digestion). These isoforms differ from each other by sialic acid content. As shown in the Examples, this is demonstrated by isolating 10 of these isoforms by preparative IEF and determining the sialic acid content of five of them. Of the isoforms assayed for sialic acid content, it is found that the five isoforms contained either 9, 10, 11, 12 or 13 sialic acid residues.

There is a relationship between the relative in vivo specific activity of erythropoietin and number of sialic acid residues per erythropoietin molecule from the isoforms 5 through 11 (each isoform is designated herein by the number of sialic acids per erythropoietin molecule). Isoforms 11 through 14 have approximately the same relative in vivo specific activity. Isoforms 5–14 are assayed for in vivo activity by the exhypoxic polycythemic mouse bioassay and the amount of each isoform present is determined by Bradford protein assay, absorbance at 280 nm or by radioimmunoassay (RIA) for erythropoietin. RIA determinations (Egrie et al. Immunobiology 172, 213, (1986)), expressed as units/ml, are divided by 212,770 units/mg erythropoietin polypeptide, the average specific activity of purified erythropoietin as determined by RIA, to give protein concentrations of isolated isoforms or isoform mixtures expressed as mg erythropoietin polypeptide/ml. As shown in the Examples, the relative in vivo specific activities increase step-wise from isoform 5 to isoform 11 (see Table 2).

The in vivo specific activities referred to herein are measurements of relative in vivo specific activities and are not measurements of absolute in vivo specific activities. For the purposes of this application, the specific activities are used only to compare relative activities of isoforms that have been assayed using the same assay, using the same conditions including the same internal standard, the same type of animals, having the same analysis of the data used to calculate specific activity, the same assay for determining protein content. It is not intended that any in vivo specific activity value reported for any isoform represents an inherent or absolute value for that isoform.

The subject invention provides erythropoietin isoforms. The specific isoforms of erythropoietin obtained in accordance with the present invention, and their properties, may vary depending upon the source of the starting material. For example, the isoforms of urinary derived human erythropoietin are different than the isoforms of recombinant erythropoietin. In a preferred embodiment, the invention relates to an erythropoietin isoform having a specific number (i.e. a fixed number greater than 0) of sialic acids per erythropoietin molecule, said number selected from the group consisting of 1–14. Advantageously said number is 9, 10, 11, 12, 13, or 14. In another embodiment, said number is greater than 14, advantageously 16–23.

This invention also provides compositions comprising two or more erythropoietin isoforms. In one embodiment the compositions comprise a mixture of isoforms having greater than a predetermined number of sialic acids per erythropoietin molecule, e.g. greater than 11 sialic acids per erythropoietin molecule, or greater than 12 sialic acids per molecule, e.g. a mixture of isoforms 12, 13 and 14. In another embodiment the compositions comprise mixtures of isoforms having a predetermined number of sialic acids per erythropoietin molecule, e.g. less than 12, but greater than 8 sialic acids per molecule as in, for example, a mixture of isoforms 9, 10, and 11. The invention also provides for compositions of erythropoietin isoforms wherein the relative amounts of the isoforms are the same or different. For example, a mixture of isoforms 9, 10 and 11 could have the isoforms present in a variety of ratios such as 1:1:1, 2:3:1 or 20:20:1.

Advantageously, the compositions comprise mixtures of less than four isoforms, for example a mixture of isoforms 11, 12, and 13, or a mixture of 12 and 14, or a mixture of 7 and 13.

In order to produce mixtures of erythropoietin isoforms, this invention also provides methods of isolating selected erythropoietin isoforms simultaneously. These methods include isolation of individual isoforms by techniques such as preparative isoelectric focusing or preparation of mixtures of isoforms having a predetermined number of sialic acids per molecule (for example, greater than 11) by techniques such as ion exchange chromatography or chromatofocusing. All of these techniques have as their basis the separation of proteins according to charge.

In general, ion exchange chromatography and chromatofocusing involve application of either crude human erythropoietin (cell conditioned media) or purified material to a column resin under conditions that permit binding of some or all of the erythropoietin isoforms to the resin. For crude erythropoietin preparations, it is preferable to apply the protein to the column at about pH 7 while for purified preparations the protein can be applied to the column at pH 7 down to about pH 4. After washing the column with buffer at about pH 4, those erythropoietin isoforms that remain bound on the ion exchange column are eluted by increasing the pH and the salt concentration of the buffer or by applying a gradient of decreasing pH and increasing ionic strength at about pH 4. For chromatofocusing, the isoforms are eluted from the column by a gradient of decreasing pH or by washing the column with a high concentration of salt.

One embodiment the invention relates to mammalian (e.g., Chinese Hamster Ovary, CHO) host cells which preferentially synthesize erythropoietin isoforms having greater than a specific number, e.g. greater than 10 sialic acids per molecule. Erythropoietin molecules have N-linked or O-linked oligosaccharides structures which can limit the sialic acid content of the molecule. For example, tetraantennary (four-branched) N-linked oligosaccharides most commonly provide four possible sites for sialic acid attachment while bi- and triantennary oligosaccharide chains, which can substitute for the tetraantennary form at asparagine-linked sites, commonly have at most only two or three sialic acids attached. O-linked oligosaccharides commonly provide two sites for sialic acid attachment. Thus, erythropoietin molecules can accommodate a total of 14 sialic acid residues provided all three N-linked oligosaccharides are tetraantennary. Mammalian cell cultures are screened for those cells that preferentially add tetraantennary chains to recombinant erythropoietin, thereby maximizing the number of sites for sialic acid attachment.

The N-linked oligosaccharides of urinary erythropoietin contain sialic acid in both an $\alpha$ 2,3 and an $\alpha$ 2,6 linkage to galactose (Takeuchi et al. J. Biol. Chem. 263, 3657(1988)). Typically the sialic acid in the $\alpha$ 2,3 linkage is added to galactose on the mannose $\alpha$ 1,6 branch and the sialic acid in the $\alpha$ 2,6 linkage is added to the galactose on the mannose $\alpha$ 1,3 branch. The enzymes that add these sialic acids ($\beta$-galactoside $\alpha$ 2,3 sialyltransferase and $\beta$-galactoside $\alpha$ 2,6 sialyltransferase) are most efficient at adding sialic acid to the mannose $\alpha$ 1,6 and mannose $\alpha$ 1,3 branches respectively.

Dihydrofolate reductase (DHFR) deficient Chinese Hamster Ovary (CHO) cells are a commonly used host cell for the production of recombinant glycoproteins including recombinant erythropoietin. These cells do not express the enzyme $\beta$-galactoside $\alpha$ 2,6 sialyltransferase and therefore do not add sialic acid in the $\alpha$ 2,6 linkage to N-linked oligosaccharides of glycoproteins produced in these cells. (Mutsaers et al. Eur. J. Biochem. 156, 651 (1986); Takeuchi et al. J. Chromatogr. 400, 207 (1987)). Consequently, recombinant erythropoietin produced in CHO cells lacks sialic acid in the 2,6 linkage to galactose (Sasaki et al. (1987), supra; Takeuchi et al. (1987), supra). In another embodiment of the subject invention, the erythropoietin used to produce the isoforms is made in CHO cells that are transfected with a functional $\beta$-galactoside $\alpha$ 2,6 sialyltransferase gene to give incorporation of sialic acid in $\alpha$ 2,6 linkage to galactose. See Lee et al. J. Biol. Chem. 264, 13848 (1989), hereby incorporated by reference, for a disclosure of techniques for creating modified CHO cells or other mammalian host cells.

Also encompassed by the invention are certain analogs of human erythropoietin. As used herein the phrase "analog of human erythropoietin" refers to erythropoietin with one or more changes in the amino acid sequence of human erythropoietin which result in an increase in the number of sites for sialic acid attachment. Analogs are generated by site-directed mutagenesis having additions, deletions, or substitutions of amino acid residues that alter sites that are available for glycosylation. Such analogs have a greater number of carbohydrate chains than human erythropoietin.

Analogs that result in increased biological activity are constructed by increasing the sialic acid content of the erythropoietin molecule. Analogs having levels of sialic acid greater than that found in human erythropoietin are generated by adding glycosylation sites which do not perturb the secondary or tertiary conformation required for biological activity. Advantageously, the analog of human erythropoietin has 1, 2 or 3 additional sites for N-glycosylation or O-glycosylation. For example, a leucine at position 69 is replaced by an asparagine to give the sequence Asn-Leu-Ser, which serves as a fourth site for N-glycosylation. Such a change can commonly provide up to four additional sialic acids per molecule. Examples of other changes that generate additional N- or O-glycosylation sites are alanines at positions 125 and 127 to asparagine and serine, respectively, alanine at position 125 to threonine and alanines at positions 124 and 125 to proline and threonine, respectively. As will be appreciated by those skilled in the art, the subject invention includes many other analogs of human erythropoietin having additional sites for glycosylation.

Also comprehended by the invention are pharmaceutical compositions comprising a therapeutically effective amount of a specific isoform or mixture of isoforms together with a suitable diluent, adjuvant and/or carrier useful in erythropoietin therapy. A "therapeutically effective amount" as used herein refers to that amount which provides therapeutic effect for a given condition and administration regimen. The administration of erythropoietin isoforms is preferably by parental routes. The specific route chosen will depend upon the condition being treated. The administration of erythropoietin isoforms is preferably done as part of a formulation containing a suitable carrier, such as human serum albumin, a suitable diluent, such as a buffered saline solution, and/or a suitable adjuvant. The required dosage will be in amounts sufficient to raise the hematocrit of patients and will vary depending upon the severity of the condition being treated, the method of administration used and the like.

The following examples are offered to more fully illustrate the invention, but are not to be construed as limiting the scope thereof. The erythropoietin standard used in the in vivo bioassays employed in the Examples is a recombinant erythropoietin standard that was standardized against a partially purified urinary erythropoietin standard. Thus, only relative in vivo specific activities are being measured. Also the in vivo specific activities are expressed in "units/ml", "units/mg" and units/$A_{280}$" and not as "IU/ml", "IU/mg" and IU/$A_{280}$", because the erythropoietin standard employed has not been directly correlated to any existing international standard.

EXAMPLE 1

Isolation of Recombinant Erythropoietin Isoforms

Recombinant erythropoietin is produced as described in Lin, supra. Recombinant erythropoietin used as starting material for the first and third isoform isolations is purified according to the procedure described in Example 2 of commonly owned Lai et al., supra. Starting material for the second and fifth isoform isolation is purified according to Lai et al. supra using the modification of Q-Sepharose chromatography. These preparations contain a mixture of isoforms of recombinant erythropoietin having the same amino acid sequence as urinary derived human erythropoietin and contain predominantly isoforms 9 to 14. Starting material for the fourth isoform preparation is the material which elutes during the 5 mM acetic acid/1 mM glycine/6M urea wash of the anion exchange column in Example 2 of Lai et al. This fraction contains isoforms with less than or equal to 9 sialic acids and was further purified by gel filtration chromatography as described in Example 2 of Lai et al. prior to use in the preparative isoelectric focusing procedure. The sixth isoform preparation used as its starting material a purified preparation of recombinant erythropoietin having from 4 to 13 sialic residues. This material was purified as per Example 2 of Lai et al. except for a modification to the ion exchange column (elution of the recombinant erythropoietin with a sodium chloride gradient at pH 8.4 and omission of the acetic acid/urea wash) which results in retention of most of the isoforms present in the starting material.

Six different preparations of individual isoforms are carried out by preparative isoelectric focusing in a granulated gel bed (Ultrodex, LKB) essentially as per LKB Application Note 198. Pharmalyte (Pharmacia) 2.5–5 ampholytes (Pharmacia) are used and the gel bed contains 5M urea.

In the first preparation, approximately 20 mg of recombinant erythropoietin in 6.8 ml of 20 mM sodium citrate/100 mM sodium chloride, pH 7.0 are applied to the gel and focused at 8 watts for approximately 16 hours. After isoelectric focusing, the isoform bands in the gel are visualized by a paper contact print of the gel bed. The print is made and then fixed by soaking in 3 changes (approximately 10 minutes each, room temperature) of fixing solution (40% methanol/10% acetic acid/10% TCA/3.5% sulfosalicylic acid), subjected to one change (approximately 10 minutes) of 40% methanol/10% acetic acid (30°–60° C.), stained for 15 minutes at 60° C. in 0.125% Coomassie Blue R-250/40% methanol/10% acetic acid, and then destained in 7.5% methanol/10% acetic acid in order to visualize the separated isoforms. The region of the granulated gel bed containing the isoforms (~50% of the resin) is removed, water is added (~16 ml), and the slurry is poured into a 5.5×24.5 inch tray and evaporated to ~40 g net weight. This preparation is focused for a second time and a contact print of the gel bed is made as before. The portion of gel containing each of the six discernible isoforms is removed from the gel bed.

In order to elute the isoforms from the gel, a solution containing 10 mM Tris-HCl, pH 7.0/5 mM Chaps is added to each isoform to generate a slurry. The slurries are placed in small columns and washed with the Tris-Chaps buffer. The flow throughs are collected and applied separately to small columns (open column configuration) containing Vydac C4 reversed phase resin equilibrated in 20% ethanol/10 mM Tris-HCl, pH 7.0. The columns are developed stepwise with 20% ethanol/10 mM Tris-HCl, pH 7.0, 35% ethanol/10 mM Tris-HCl, pH 7.0, and 65% ethanol/10 mM Tris-HCl, pH 7.0. The fraction eluting at 65% ethanol/10 mM Tris is diluted 1:1 with 10 mM Tris-HCl, pH 7.0 and subjected to concentration and then buffer exchanged to 10 mM Tris-HCl, pH 7.0 using a Centricon-10 (Amicon) microconcentrator. Analytical isoelectric focusing of this preparation is performed essentially as described in LKB technical note 250 using Servalyte 3–5 ampholines (Serva) in a polyacrylamide gel containing 5M urea.

In a second preparation, approximately 26 mg of recombinant erythropoietin in 6.5 ml of deionized water are applied to the gel and focused at 2.5 watts for 35 minutes and 10 watts for approximately 17 hours. The bands of focused protein, which are visible in the gel bed, are removed as 11 different pools. Each pool is brought to about 7.5 ml with deionized water and 20 ml of each of the resulting pool supernatants is subjected to analytical isoelectric focusing as described above. To each of the pools is added 5 ml of 1.5M Tris-HCl, pH 8.8 and the slurries are each placed in small columns and the liquid phase allowed to flow through. The resin is washed with approximately three volumes of 0.5M Tris-HCl, pH 7 and the rinse solution is combined with the flow through. The eluants are concentrated and buffer exchanged to 20 mM sodium citrate/100 mM sodium chloride, pH 7.0 using Amicon disposable ultrafiltration devices having a 10,000 dalton molecular weight cutoff. The concentrated solutions (approximately 0.5 ml) are then passed through a 0.22 micron cutoff cellulose acetate filter. Based upon analytical isoelectric focusing, five pools are found to contain predominantly the single isoforms 10, 11, 12, 13 and 14.

In a third preparation, approximately 30 mg of recombinant erythropoietin in 21.8 ml of distilled water is applied to the gel and focused at 2 watts for 25 minutes, 10 watts for 20 hours and 15 watts for 15 minutes. Protein bands corresponding to the individual isoforms are observed visually and removed from the gel bed. Distilled water is added to gel-isolated isoforms to generate a slurry and the resulting supernatants are analyzed by analytical isoelectric focusing. An equal volume of 1M Tris-HCl, pH 7.2 is added to each slurry, the suspensions are placed into separate small columns, and the liquid phase is allowed to flow through the column to elute the isoforms. Each flow through is concentrated and buffer exchanged to 20 mM sodium citrate/100 mM sodium chloride, pH 7.0 using Amicon disposable ultrafiltration devices having a 10,000 dalton molecular weight cutoff. An analytical isoelectric focusing gel revealed that pools containing predominantly the single isoforms 9, 10, 11, 12, 13 and 14 were obtained.

A fourth isoform preparation used as its starting material erythropoietin containing isoforms 3–9 (prepared as described above). Prior to preparative isoelectric focusing carried out essentially as described for preparations 1–3 above, the ampholytes (Pharmalyte 2.5–5) were prefractionated in a Rotofor (Bio-Rad, Richmond, Calif.) liquid phase isoelectric focusing cell to yield an ampholyte range more suitable for the lower isoelectric points of the starting material. The prefractionation was carried out by mixing 6.7 mL of Pharmalyte 2.5–5 with 15 g of urea and adding purified water to bring the volume to 50 mL. This mixture was fractionated in the Rotofor at 10 Watts, 1° C., for 5 ½ hours using 0.1M phosphoric acid and 0.1M sodium hydroxide as the anolyte and catholyte, respectively. The ampholyte fractions having measured pHs of between 4.5 and approximately 6 were used in the flat-bed isoelectric focusing.

Ampholytes were removed from the isoforms using a Centrieluter (Amicon, Danvers, Mass.) and a 10,000 MW cutoff Centricon (Amicon) using the following parameters: 0.18 Tris buffer pH 8.8, 100 Volts, 25–30 mA, for 3 hours. The isoforms were then buffer exchanged into 0.1M sodium chloride by gel filtration using Sephadex G-25 (Pharmacia). Analytical isoelectric focusing of the five resulting pools showed them to contain isoforms 4,5,6,7, and 8. Isoform 4 ran as several bands, indicating that it may have undergone some degradation.

The fifth isoform preparation was modified by the addition of a pre-focusing step to the flat bed isoelectric focusing procedure. In this modification, the protein was not added to the ampholyte/urea/gel mixture prior to electrophoresis but was added to the isoelectric focusing apparatus following generation of the pH gradient in the gel bed. Following prefocusing for 75 minutes (1500 volt-hrs) the section of gel bed from 2.25–4.25 cm from the cathode was removed, mixed with the erythropoietin solution, and added back to the gel bed. Following isoelectric focusing, isoforms 10,11, 12,13, and 14 were eluted from the gel bed and separated from the ampholytes by ultrafiltration using Centricon-10 (Amicon) devices.

The pre-focusing modification was undertaken to make the ultraviolet absorbance characteristics of the isoform preparations more similar to that of the starting recombinant erythropoietin. This improvement in spectral characteristics can be seen in the ratio of absorbance at 280 and 260 nm for the isolated isoforms. The average ratio of absorbance at 280 nm to that at 260 nm (A280/A260) for isoforms from preparations 2 and 3 (non-prefocused) is 1.36±0.11 while the average A280/A260 ratio for preparations 5 and 6 (pre-focused) is 1.68±0.20. When isoform #14 is excluded from the calculation, the average A280/A260 ratios are 1.39±0.11 and 1.74±0.09 for preparations 2 & 3 and 5 & 6, respectively. (Isoform 14 may have the most atypical spectrum because it is present in the smallest amounts and is thus more subject to interferences by trace contamination by ampholyte components or because it is nearest to the electrode during the flat bed isoelectric focusing procedure). The average A280/A260 ratio for recombinant erythropoietin prepared according to Example 2 of Lai et al. (modified as described earlier by using Q-Sepharose as the anion exchange resin) is 1.91±0.04.

As described above, the starting material for isoform preparation #6 was a recombinant erythropoietin preparation containing isoforms 4–13. The ampholytes were pre-focused in the Rotofor apparatus as per the fourth preparation. Ampholyte fractions having measured pHs of between 3.7 and 4.8 were used for the flat bed isoelectric focusing. The flat bed was pre-focused as in run #5 and isoforms 9,10,11, 12 and 13 were obtained after ultrafiltration (Centricon-10) to remove carrier ampholytes.

EXAMPLE 2

Sialic Acid Content of Recombinant Erythropoietin Isoforms

The isoforms isolated as described in Example 1 and erythropoietin purified according to procedures described in Lai et al., supra (mixture of isoforms 9 to 14) are buffer exchanged into 0.10–0.15M sodium chloride and analyzed for sialic acid content by a modification of the procedure of Jourdian et al. J. Biol. Chem. 246, 430 (1971). The sialic acid residues are cleaved from the glycoproteins by hydrolysis with 0.35M sulfuric acid at 80° C. for 30 minutes and the solutions are neutralized with sodium hydroxide prior to analysis. In order to estimate the amount of erythropoietin protein present, a Bradford protein assay (Bradford Anal. Biochem. 72, 248 (1976)) using recombinant erythropoietin having the amino acid sequence of human erythropoietin as standard is performed using the assay reagents and the micro-method procedure supplied by Bio-Rad. The results, expressed as moles of sialic acids per mole of erythropoietin, are shown in Table 1. Isoforms are designated according to the number of sialic acids per molecule and range from least acidic (Isoform 9) to most acidic (Isoform 13). Isoforms 9–13 are shown in gel lanes 6–10 of FIG. 1. Quantities of Isoform 14 are insufficient to accurately measure the sialic acid content. The sialic acid content of this isoform is inferred from its migration on IEF gels relative to other isoforms. The sialic acid content of isoforms 5–8 (preparation #4) has not been measured but is likewise inferred from their migration on IEF gels.

TABLE 1

| ERYTHROPOIETIN ISOFORM | MOLES SIALIC ACID/ MOLE ERYTHROPOIETIN |
|---|---|
| Isoform 13 | 12.9 ± 0.5 |
| Isoform 12 | 11.8 ± 0.2 |
| Isoform 11 | 11.0 ± 0.2 |
| Isoform 10 | 9.8 ± 0.3 |
| Isoform 9 | 8.9 ± 0.6 |
| Isoform Mixture (9-14) | 11.3 ± 0.2 |

EXAMPLE 3

Activity of Recombinant Erythropoietin Isoforms

The isoforms isolated as described in Example 1 are assayed by absorbance at 280 nm, by Bradford protein assay and by RIA for erythropoietin to determine the amount of recombinant erythropoietin present. The exhypoxic polycythemic mouse bioassay (Cotes et al. Nature 191, 1065 (1961)) is used to determine the relative in vivo biological activity. Quantitation of the amount of erythropoietin protein present using a radioimmunoassay for erythropoietin produced results having higher relative in vivo specific activity for certain isoforms because of an apparent decreased immunoreactivity of isoforms containing large amounts of sialic acid leading to an underestimation of the erythropoietin concentration and thus an overestimation of the relative in vivo specific activity for the most negative isoforms. Mouse bioassay determinations, expressed as units/ml, are divided by the corresponding protein concentrations to give in vivo specific activities expressed as units/mg erythropoietin polypeptide. These specific activities are shown in Table 2.

In Table 2, "n" is the number of independent isoform preparations which contribute to the specific activity value. In most cases several in vivo assays were performed on each isoform preparation. The same in vivo data contribute to the specific activity calculations for all three columns, units/mg erythropoietin polypeptide was determined by the absorbance at 280 nm, from radioimmunoassay potencies, or from Bradford protein assay results. Purified recombinant erythropoietin containing isoforms 9–14 was used as the standard in the Bradford protein assay. "n" may be less for the calculation made using the Bradford protein assay as some preparations were no longer available at the time the Bradford assays were performed.

Erythropoietin purified according to the procedures described in Lai et al., supra and containing a mixture of isoforms 9 to 14 is used as a standard for the RIAs and in vivo assays.

The relative specific activities expressed as units/mg erythropoietin polypeptide can be converted to units/$A_{280}$ by multiplying by 0.807 mg erythropoietin polypeptide/$A_{280}$. The conversion factor is derived by multiplying the extinction coefficient of erythropoietin (1.345 mg/$A_{280}$) by the protein content of the erythropoietin glycoprotein (about 60% by weight, Davis et al. Biochemistry 26, 2633 (1987)) to obtain mg erythropoietin polypeptide/$A_{280}$ (i.e., 1.345 mg erythropoietin/$A_{280}$×0.60 mg polypeptide/mg erythropoietin=0.807 mg polypeptide/$A_{280}$). In addition, specific activities expressed as units/mg erythropoietin polypeptide can be multiplied by the factor 0.60 mg polypeptide/mg erythropoietin glycoprotein to give specific activities expressed as units/mg erythropoietin glycoprotein.

TABLE 2

| Isoform | U/mG Polypeptide (Bradford Protein Assay) | n | U/mG Polypeptide (From A280) | n | U/mG Polypeptide (From RIA) | n |
| --- | --- | --- | --- | --- | --- | --- |
| 14 | 289,400 ± 3,100 | 2 | 205,800 ± 37,700 | 2 | 366,700 ± 55,900 | 2 |
| 13 | 307,600 ± 30,600 | 4 | 258,700 ± 59,500 | 5 | 337,200 ± 40,200 | 5 |
| 12 | 275,200 ± 55,600 | 4 | 258,400 ± 41,700 | 5 | 287,700 ± 42,600 | 5 |
| 11 | 282,700 ± 41,100 | 3 | 255,800 ± 67,300 | 4 | 251,400 ± 62,700 | 4 |
| 10 | 188,000 ± 1,900 | 1 | 170,300 ± 34,500 | 3 | 171,900 ± 31,600 | 3 |
| 9 | — | | 96,600 ± 46,700 | 2 | 113,600 ± 39,600 | 2 |
| 8 | 65,200 ± 3,800 | 1 | 70,600 ± 4,100 | 1 | 61,000 ± 3,500 | 1 |
| 7 | 46,200 ± 5,800 | 1 | 50,300 ± 6,300 | 1 | 42,800 ± 5,400 | 1 |
| 5 | 16,600 ± 1,700 | 1 | 18,300 ± 1,900 | 1 | 15,500 ± 1,600 | 1 |

The data in Table 2 are also presented graphically in FIGS. 2A, 2B and 2C. These data show that the relative in vivo activity of erythropoietin increases as a function of sialic acid content up until isoform #11. Isoforms 11–14 have essentially the same relative in vivo bioactivity. (This is most apparent when the concentration of isoform 14 is expressed using the Bradford assay value. The Bradford value may be more accurate for isoform 14 because of the generally low levels obtained and the resulting difficulty in determination by $A_{280}$ and the most apparent decreased reactivity in the RIA of very negative forms discussed previously). The greater relative in vivo specific activity of erythropoietin isoforms having more sialic acid is most likely due to a longer circulating half-life of these forms. Isoforms 9 and 13 were labeled with radioactive iodine ($^{125}$I) and their rate of clearance in rats was determined. The half-life in circulation was significantly longer for isoform 13 than for isoform 9.

EXAMPLE 4

Selection of Recombinant Erythropoietin Isoform Mixtures by O-Sepharose Chromatography Cell conditioned media from the production of recombinant erythropoietin according to the procedures described in Lin, supra are concentrated and diafiltered against 10 mM Tris, pH 7.2. Protein concentration is determined by the Bradford microprotein assay using bovine serum albumin as a standard. 19.6 ml of the solution containing 40 mg of total protein is made 20 μM in $CuSO_4$, filtered through a 0.45 micron cutoff filter and loaded onto a 4 ml bed volume (1.05 cm height×2.2 cm diameter) column packed with Q Sepharose Fast Flow (Pharmacia) which has been equilibrated with 10 mM Tris, pH 6.8 to 7.0 at 4° C. After sample application, the column is washed with two column volumes of the same buffer. The column flow rate is about 1 ml/min. Six separate columns are set up using this procedure to select defined erythropoietin isoform mixtures.

Columns are washed with 6 to 9 column volumes of a low pH buffer consisting of: Column #1, 150 mM acetic acid, 1 mM glycine, 20 μM $CuSO_4$, 6M urea adjusted to pH 4.7 with NaOH; Column #2, 200 mM acetic acid, 1 mM glycine, 20 μM $CuSO_4$, 6M urea adjusted to pH 4.7 with NaOH; Column #3, 250 mM acetic acid, 1 mM glycine, 20 μM $CuSO_4$, 6M urea adjusted to pH 4.7 with NaOH; Column #4, 300 mM acetic acid, 1 mM glycine, 20 μM $CuSO_4$, 6M urea adjusted to pH 4.7 with NaOH; Column #5, 150 mM acetic acid, 1 mM glycine, 20 μM $CuSO_4$, 6M urea; Column #6, 300 mM acetic acid, 1 mM glycine, 20 μM $CuSO_4$, 6M urea. The pH of the columns is increased to approximately pH 7 by washing each one with 8 to 11 column volumes of 10 mM Tris-HCl, 55 mM NaCl, 20 μM $CuSO_4$, pH 7. The defined erythropoietin isoform mixtures are eluted from the columns by washing with 10 mM Tris-HCl, 140 mM NaCl, 20 μM $CuSO_4$, pH 7.0.

The eluted isoform pools from each column are concentrated and solvent exchanged into water using an Amicon Centricon-10 microconcentrator. The results of analytical isoelectric focusing of these concentrated pools are shown in FIG. 3. Gel lanes 1–6 represent defined erythropoietin isoform mixtures eluted from column 1–6, respectively. The "isoform mixture" shown in the far right gel lane of FIG. 3 represents cell media which is applied to a Q-Sepharose column as described above, the column is washed with 5 mM acetic acid, 1 mM glycine, 20 μM $CuSO_4$, 6M urea, and the erythropoietin isoform mixture is eluted from the column using the procedures described above. This eluted mixture of isoforms is further purified according to the procedures described in Lai et al., supra prior to analytical isoelectric focusing.

EXAMPLE 5

Figure 4:
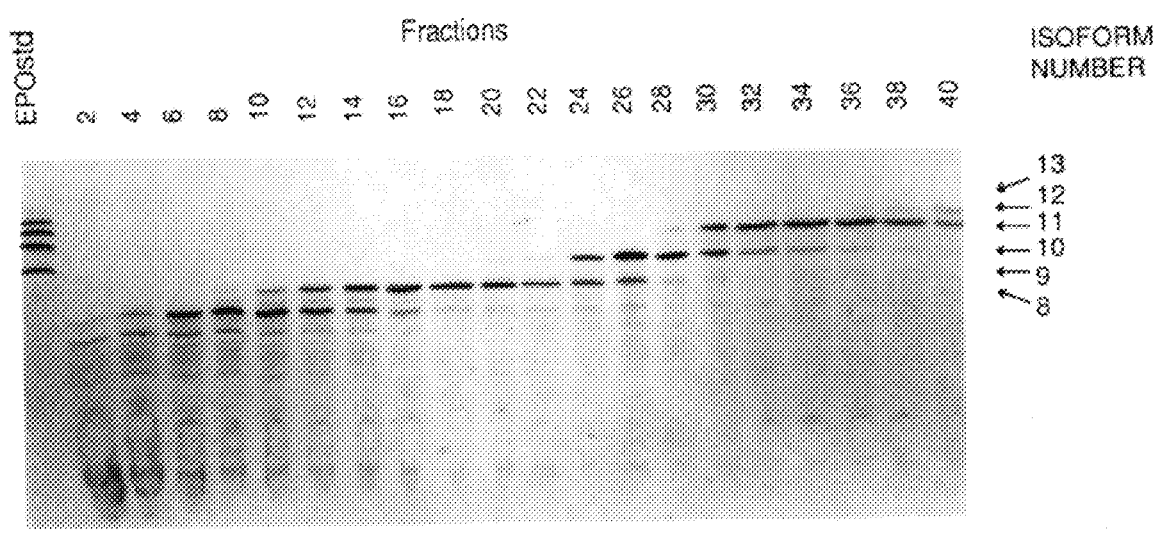
FIG. 4 shows the separation of erythropoietin isoforms 8 to 12 achieved by subjecting cell conditioned medium applied to a column of Q-Sepharose to a gradient of decreasing pH and increasing ionic strength. Aliquots of even numbered fractions from Fraction 2 to Fraction 40 were subjected to analytical isoelectric focusing. Purified recombinant erythropoietin containing a mixture of isoforms obtained using procedures described in Example 2 of Lai et al. supra, except that DEAE-Agarose chromatography is replaced by Q-Sepharose chromatography, is also shown in the far left lane of the gel.

Fractionation of Recombinant Erythropoietin Isoforms Using a Low pH Gradient on O-Sepharose In another procedure, erythropoietin isoforms are separated using a gradient of decreasing pH and increasing ionic strength. The concentrated diafiltered erythropoietin containing media is loaded to a column of Q-Sepharose at a ratio of approximately 40 mg total protein/mL gel. The column is then washed with approximately two column volumes of 10 mM Tris HCl, pH 7.0 and then approximately 10 column volumes of 2 mM acetic acid/1 mM glycine/20 μM $CuSO_4$/ 6M urea (pH approximately 4.8) to remove contaminating proteins and erythropoietin isoforms containing less than approximately 7 sialic acid residues. Isoforms containing from approximately 8 to approximately 12 sialic acids are eluted from the column using a gradient starting at approximately 2 mM acetic acid in 6M urea/1 mM glycine/20 μM $CuSO_4$ and running to 40 mM acetic acid/6M urea/1 mM glycine/20 μM $CuSO_4$ (pH approximately 4). The total volume of the gradient is approximately 40 column volumes and fractions of approximately one column volume each are collected into vessels containing a volume of Tris buffer sufficient to bring the pH into the range of 6–8.5 so as to avoid long term exposure of the collected fractions to low pH. Aliquots of the fractions are subjected to analytical isoelectric focusing to monitor the separation. FIG. 4 shows the separation of isoforms 8–11 which may be achieved by this procedure. Isoforms 12–14 which remain bound to the column at the end of the gradient are eluted by washing with a buffer consisting of 10 mM TrisHCl, 140 mM NaCl, 20 µM $CuSO_4$ (pH 7.0). The isoforms (separated during the gradient or eluted by the sodium chloride solution) are freed of contaminating proteins by reverse phase chromatography followed by gel filtration chromatography as described in Example 2 of Lai et al.

EXAMPLE 6

Analogs of Human Erythropoietin Having Additional Glycosylation Sites.

A. Construction of Human Erythropoietin Analogs.

Figure 6A:
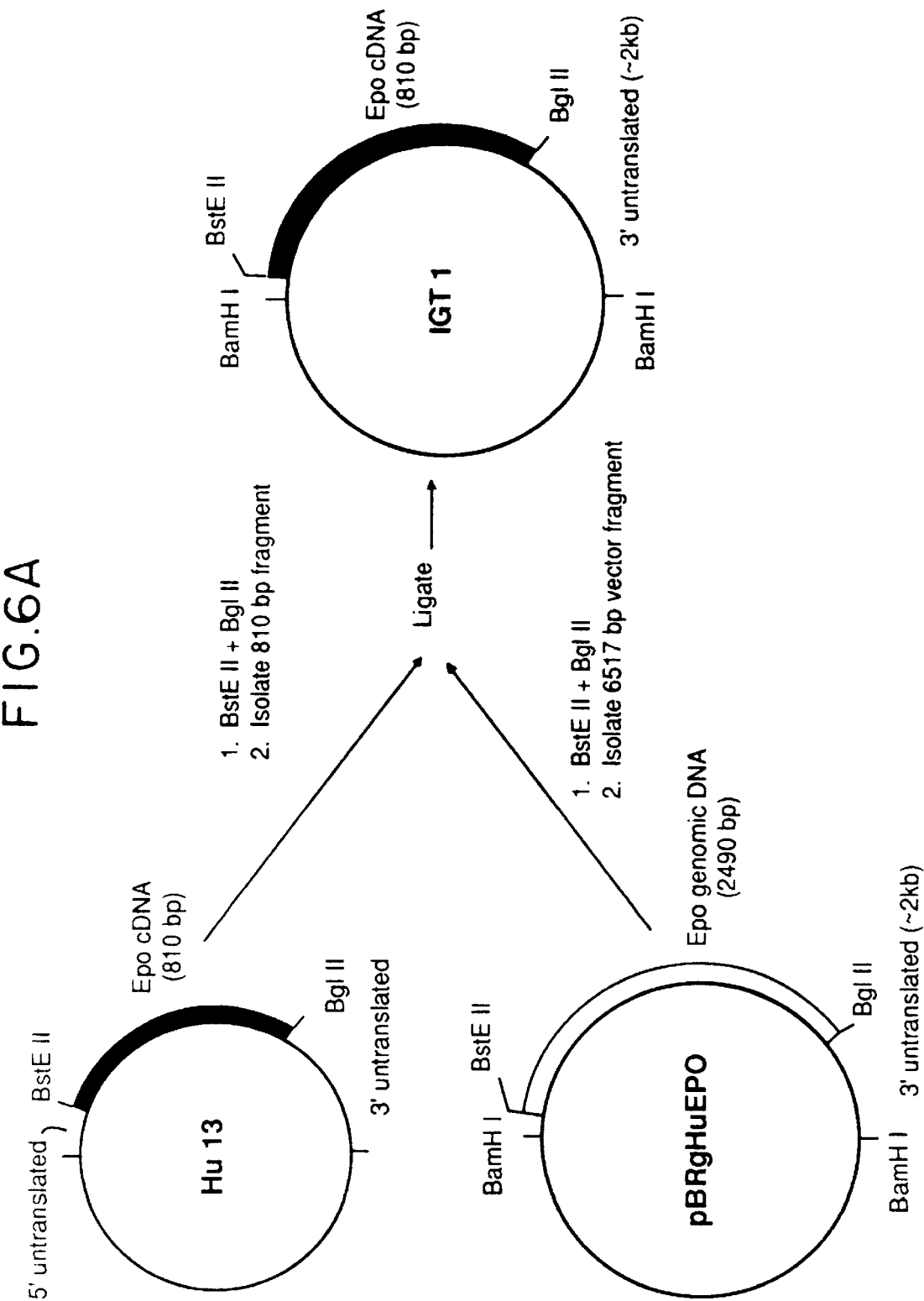
FIG. 6A, FIG. 6B, and FIG. 6C show the series of cloning steps used in generating plasmids for the construction and analysis of analogs of human erythropoietin. These analogs have amino acids altered as shown in FIG. 5 which provide additional glycosylation sites.
Figure 6B:
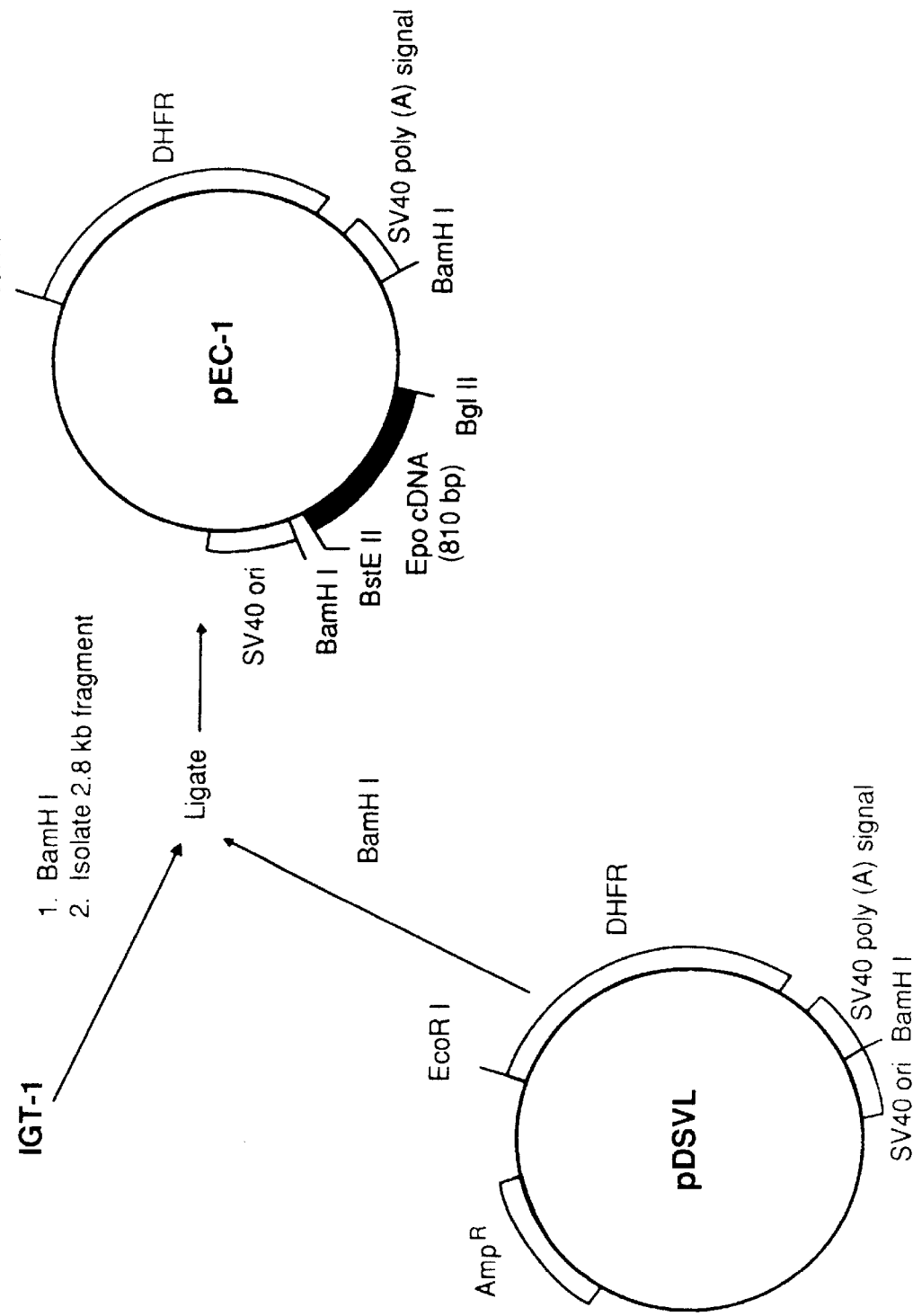
Figure 6C:
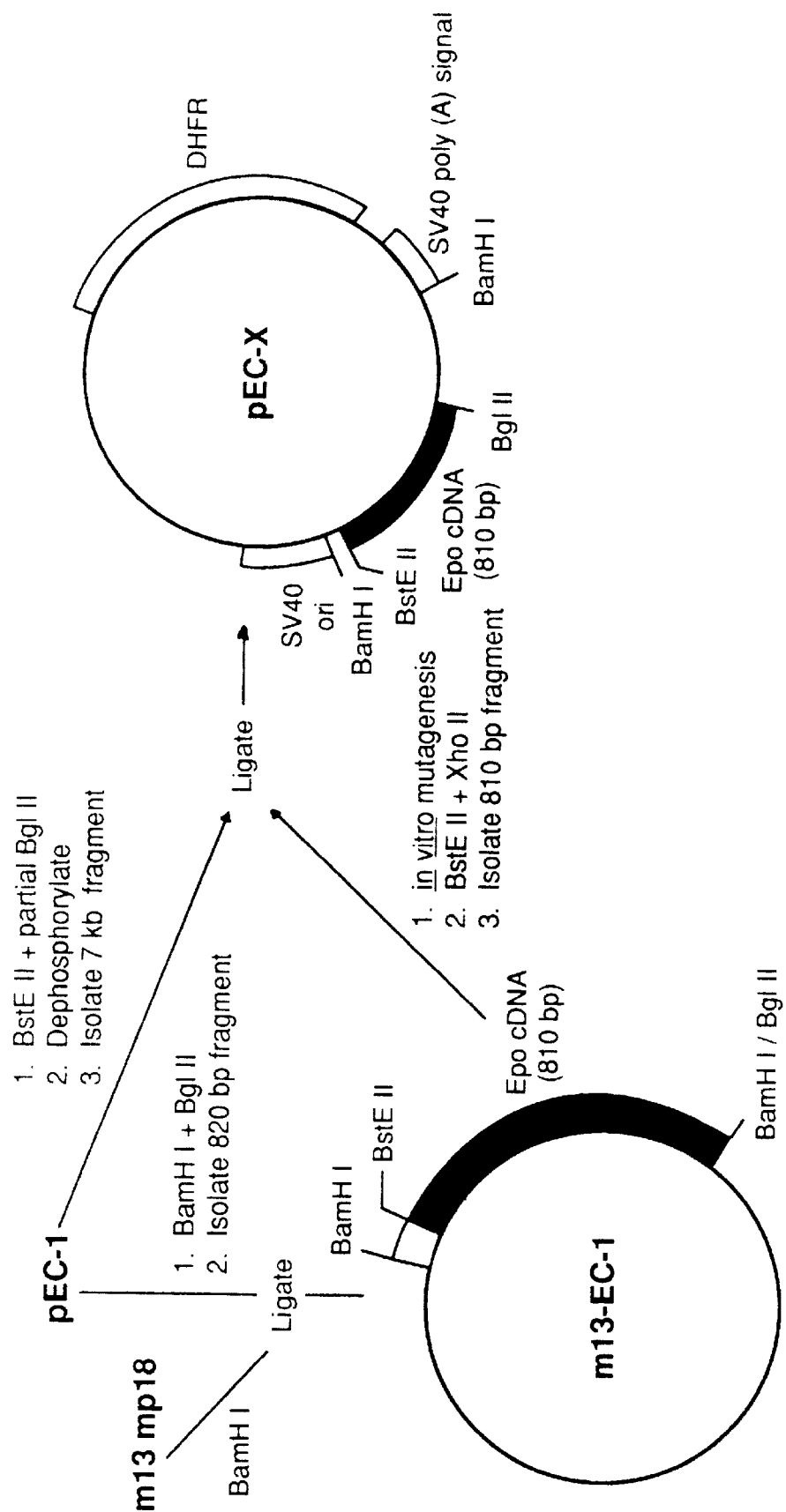

The locations of existing and proposed carbohydrate attachment sites within the erythropoietin amino acid sequence are shown in FIG. 5 and the procedure for generating these additional glycosylation sites is summarized in FIGS. 6A–C and described below.

The following oligonucleotide primers were synthesized for use in in vitro mutagenesis:
[$Asn^4$, $Ser^6$] EPO: 5' CGCCCACCA<u>AAC</u>CTC <u>AGC</u>TGTGACAGCCGA 3'
[$Asn^9$, $Ser^{11}$] EPO: 5' ATCTGTAC<u>AAC</u>CGA <u>AGC</u>CTGGAGAGGT 3'
[$Asn^{69}$]EPO: 5' GGGCCTGGCC<u>AAC</u>CTGTCGGAAG 3'
[$Asn^{124}$] EPO: 5' TCCCCTCCAGAT <u>AAT</u>GCCTCAGCTGC 3'
[$Asn^{125}$, $Ser^{127}$] EPO: 5' CAGATGCG<u>AAC</u>TCA <u>TCT</u>GCTCCAC 3'
[$Asn^{163}$, $Ser^{165}$] EPO: 5' AGGCCTGCAGG<u>AAT</u>GGG <u>AGC</u>AGATGACCAGGTG 3'
[$Thr^{125}$] EPO: 5' TCCAGATGCG<u>A</u>CCTCAGCTGCTC 3'
[$Pro^{124}$, $Thr^{125}$] EPO: 5' CCTCCAGAT<u>C</u>CG <u>A</u>CCTCAGCTGC 3'

The underlined codons show the mismatched regions where the amino acids indicated in brackets replace the wild-type amino acids.

[$Asn^4$, $Ser^6$] EPO was constructed to add an N-glycosylation site at Asn 4. [$Asn^9$, $Ser^{11}$] EPO was constructed to add an N-glycosylation site at Asn 9. [$Asn^{69}$] EPO was constructed to add an N-glycosylation site at Asn 69. [$Asn^{125}$, $Ser^{127}$] EPO was constructed to add an N-glycosylation site at Asn 125. [$Thr^{125}$] EPO and [$Pro^{124}$, $Thr^{125}$] EPO were constructed to add an O-glycosylation site at Thr 125.

The following oligonucleotide primers are synthesized for use in in vitro mutagenesis:
[$Asn^{69}$, $Thr^{71}$] EPO: 5' GGGCCTGGCC<u>AAC</u>CTGA<u>C</u> <u>A</u>GAAGCTGTC 3'
[$Ser^{68}$, $Asn^{69}$, $Thr^{71}$] EPO: 5' CAGGGCCTG <u>TCCAAC</u>CTGA<u>C</u>AGAAGCTGTC 3'
[$Asn^{125}$, $Thr^{127}$] EPO: 5' CAGATGCG<u>AAC</u>TCAA <u>CG</u>GCTCCAC 3'
[$Asn^{125}$, $Thr^{127}$, $Thr^{131}$] EPO: 5'ATGCG<u>AAC</u>TCAA <u>CG</u>GCTCCACTC<u>A</u>C<u>A</u>ACAATCACT 3'
[$Pro^{124}$, $Asn^{125}$, $Ser^{127}$] EPO: 5' CCAGAT<u>CC</u>AA<u>AT</u>TCA <u>TCT</u>GCTCCACTC 3'
[$Pro^{124}$, $Asn^{125}$, $Thr^{127}$] EPO: 5' CCAGAT<u>CC</u>AA<u>AT</u>TCA <u>AC</u>AGCTCCACTC 3'
[$Thr^{125}$, $Thr^{126}$] EPO: 5' CCAGATGCG <u>ACAAC</u>AGCTGCTCCA 3'
[$Pro^{124}$, $Thr^{125}$, $Thr^{126}$, $Thr^{131}$] EPO:

Starting from [$Pro^{124}$, $Thr^{125}$] EPO cDNA, the oligonucleotide primer 5' AGATCCGACC<u>A</u>C <u>C</u>GCTGCTCCAC 3' is used to generate [$Pro^{124}$, $Thr^{125}$, $Thr^{126}$] EPO. The oligonucleotide primer 5'TGCTCCACTC <u>AC</u>AACAATCACTG 3' is then used to generate [$Pro^{124}$, $Thr^{125}$, $Thr^{126}$, $Thr^{131}$] EPO.

[$Asn^{69}$, $Thr^{71}$] EPO and [$Ser^{68}$, $Asn^{69}$, $Thr^{71}$] EPO are constructed to add an N-glycosylation site at Asn 69 and to enhance N-glycosylation at that site. [$Asn^{125}$, $Thr^{127}$] EPO, [$Asn^{125}$, $Thr^{127}$, $Thr^{131}$] EPO, [$Pro^{124}$, $Asn^{125}$, $Ser^{127}$] EPO and [$Pro^{124}$, $Asn^{125}$, $Thr^{127}$] EPO are constructed to add an N-glycosylation site at Asn 125 and to increase glycosylation at that site. [$Thr^{125}$, $Thr^{126}$] EPO and [$Pro^{124}$, $Thr^{125}$, $Thr^{126}$, $Ser^{131}$] EPO are constructed to add an O-glycosylation site at Thr 125 and to increase glycosylation at that site.

The source of erythropoietin DNA for in vitro mutagenesis was plasmid Hul3, a human erythropoietin cDNA clone in pUC 8 (Law et al. Proc Natl. Acad. Sci. 83, 6920 (1986)). Plasmid DNA derived from Hu13 was digested with BstEII and BglII restriction enzymes, the resulting DNA fragments were subjected to agarose gel electrophoresis, and the 810 base pair (bp) erythropoietin DNA fragment was isolated from the gel using a GeneClean™ kit and procedures supplied by the manufacturer (BIO 101, Inc.). Plasmid pBRgHuEPO contains the erythropoietin genomic gene as a BamHI fragment inserted into a derivative of pBR322, as described in commonly owned Lin patent, supra. pBRgHuEPO was also digested with BstEII and BglII and the 6517 bp vector fragment was recovered. Ligation of the two fragments results in IGT1. To construct pEC-1, pDSVL (described in commonly owned Lin patent, supra, and shown in FIG. 5B) was digested with BamHI and the isolated 2.8 kilobase (kb) BamHI fragment from IGT1 containing erythropoietin cDNA was ligated into it.

In order to generate single-stranded DNA for in vitro mutagenesis, pEC-1 was digested with BamHI and BglII and the 820 bp erythropoietin cDNA fragment was isolated. It was ligated into the BamHI site of m13mp18 to give m13-EC-1. Single stranded DNA was recovered from supernatants of E. coli strain RZ1032 infected by m13-EC-1 as described by Kunkel et al. Methods in Enzymol. 154, 367 (1987) and Messing, Methods in Enzymol. 101, 20 (1983). For in vitro mutagenesis approximately 1 µg of single-stranded DNA and 0.2 pmole of one of the synthetic primers described above were mixed with 6 ml of buffer (250 mM Tris pH 7.8, 50 mM $MgCl_2$, and 50 mM dithiothreitol). For annealing of the primer to the template, the reaction volume was adjusted to 10 µl with water, the mixture was heated to 65° C. for 5 minutes and then allowed to cool to room temperature. For the elongation reaction 2.5 ml of each of dTTP, dATP, dGTP, dCTP and ATP (all at 10 µM) were added, followed by 1 µl (1 unit) of E. coli DNA polymerase (Klenow fragment) and 1 µl (1 unit) of T4 DNA ligase. The mixture was then incubated overnight at 14° C. and used to transform E. coli JM 109 (Yanisch-Perron et al. Gene 33, 103 (1985)) as described (Messing, supra).

To identify mutant clones by differential hybridization, plaques on nutrient agar were transferred to Gene Screen filters (New England Nuclear). The filters were dried under a heat lamp and then incubated for one hour in 6×SSC containing 1% SDS at 60° C. For the hybridization, the oligonucleotide primer above (8 pmoles) was end-labeled with T4 polynucleotide kinase and γ 32p-labeled ATP and incubated with the filters overnight in 6×SSC, 0.5% SDS and 100 mg/ml salmon sperm DNA at 37° C. for the [$Asn^{124}$] mutation, 55° C. for the [$Asn^4$, $Ser^6$] mutation, 65° C. for the [$Thr^{125}$] and the [$Pro^{124}$, $Thr^{125}$] mutations, and 70° C. for the [$Asn^9$, $Ser^{11}$] and [$Asn^{163}$, $Ser^{165}$] mutations.

The next day, the filters were washed three times with 6×SSC at room temperature and subjected to autoradiography. If necessary, the filters were then washed with 6×SSC at increasing temperatures until little or no hybridization was detected to plaques having the wild-type erythropoietin cDNA sequence. Clones that gave positive hybridization signals under these conditions were identified and retransfected into JM109 to isolate a pure clone. Dideoxy chain termination sequence analysis indicated that the mutations to asparagine, serine threonine and proline residues were present.

Double stranded m13 EC-1 DNAs carrying the [Asn$^4$, Ser$^6$], [Asn$^9$, Ser$^{11}$], [Asn$^{69}$], [Asn$^{124}$], [Asn$^{125}$, Ser$^{127}$], [Asn$^{163}$, Ser$^{165}$][Thr$^{125}$], and [Pro$^{124}$, Thr$^{125}$] changes were recovered from JM109 transfected cells by the boiling method (Holmes et al. Anal. Biochem 117, 193 (1981)). The DNAs were digested with BstEII and XhoII and the 810 bp erythropoietin DNA fragments were isolated. pEC-1 were digested with BstEII followed by a partial digestion with BglII and the 5' termini of the resulting fragments are dephosphorylated with bacterial alkaline phosphatase in 10 mM Tris, pH 8 at 60° C. for 60 minutes. The 7 kb vector fragment lacking the 810 bp BstEII-BglII fragment was isolated and ligated to the erythropoietin fragments above. The resulting plasmids (designated pEC-X where X identifies the particular mutation) contain human erythropoietin with altered amino acid residues at the indicated positions.

cDNA clones of the human erythropoietin sequence and analogs corresponding to [Asn4, Ser6], [Asn9, Ser11], [Asn$^{69}$], [Asn$^{124}$], [Asn$^{125}$, Ser$^{127}$], [Asn$^{163}$, Ser$^{165}$], [Thr$^{125}$] and [Pro$^{124}$, Thr$^{125}$] erythropoietin cDNA clones were transferred into COS-1 cells (ATCC No. CRL-1650) by electroporation. COS-1 cells were harvested from semiconfluent dishes, washed with medium (Dulbecco's modified essential medium containing 5% fetal calf serum and 1% L-glutamine/penicillin/streptomycin (Irvine Scientific)) and resuspended at 4×10$^6$ cells/ml. One ml of cells was transferred to an electroporation cuvette (Bio-Rad) and electroporated with a Bio-Rad Gene Pulser™ at 25 μFarads and 1600 volts in the presence of 100 to 200 μg of carrier DNA and 2 to 20 μg of plasmid DNA encoding the erythropoietin analog. The electroporated cells were plated at 2×10$^6$ cells per 60 mm tissue culture dish in 5 ml of medium. Two to four hours after plating the medium was replaced with 5 ml of fresh medium. The conditioned medium was collected 3 to 5 days after electroporation.

B. Assays for erythropoietin analog activity

RIAs were performed according to Egrie et al., supra. The in vivo biological activity of erythropoietin analogs was determined by the exhypoxic polycythemic mouse bioassay (Cotes et al., supra).

In vitro erythropoietin activity was determined by the erythroid colony forming assay as described by Iscove et al. J. Cell Physiol. 83, 309–320 (1974) with modifications. The mononucleated cells from human bone marrow cells were partially purified on a ficoll-paque cushion and washed in Iscove medium before plating to remove the adherent cells. The culture medium contained 0.9% methyl cellulose and did not include any bovine serum albumin. The erythroid colonies are scored after 8 to 10 days of culture.

The erythropoietin analogs transfected and expressed in COS cells as described in Section A were analyzed in crude COS cell supernatants by RIA and by the erythroid colony forming assay. Human sequence erythropoietin has an in vitro activity that is comparable to the RIA activity as determined by the above-mentioned assays. The analogs [Asn$^{69}$] EPO, [Asn$^{125}$, Ser$^{127}$] EPO, [Thr$^{125}$] EPO and [Pro$^{124}$, Thr$^{125}$] EPO exhibited an in vitro activity that is comparable to the RIA activity and gave evidence of having additional carbohydrate chains (as determined in Section C). These analogs are analyzed further by transfecting a cDNA clone encoding the erythropoietin analog into CHO cells, purifying the erythropoietin analog and measuring the in vivo biological activity of the purified analog.

C. Western Blot Analysis

A volume of supernatant containing 5–20 units from COS cells transfected with erythropoietin analog cDNAs as described in Section A was immunoprecipitated overnight at room temperature with a rabbit anti-erythropoietin polyclonal antibody. 20–80 μl of 1:1 Protein A-Sepharose in phosphate buffered saline (PBS) was added to the immunoprecipitate and allowed to incubate for one hour at room temperature. The samples were centrifuged, washed with PBS and, where indicated, the pellet was treated with N-glycanase to remove N-linked carbohydrate chains. The samples were analyzed by 15% SDS-polyacrylamide gel electrophoresis, transferred to nitrocellulose and subjected to Western analysis as described (Burnette et al. Anal. Biochem. 112, 195–203 (1981); Elliot et al. Gene 79, 167–180 (1989)) using a mixture of mouse anti-erythropoietin monoclonal antibodies. One such antibody, 9G8A, is described in Elliot et al. (1989) Blood 74, Supp. 1, A. 1228.

Figure 7:
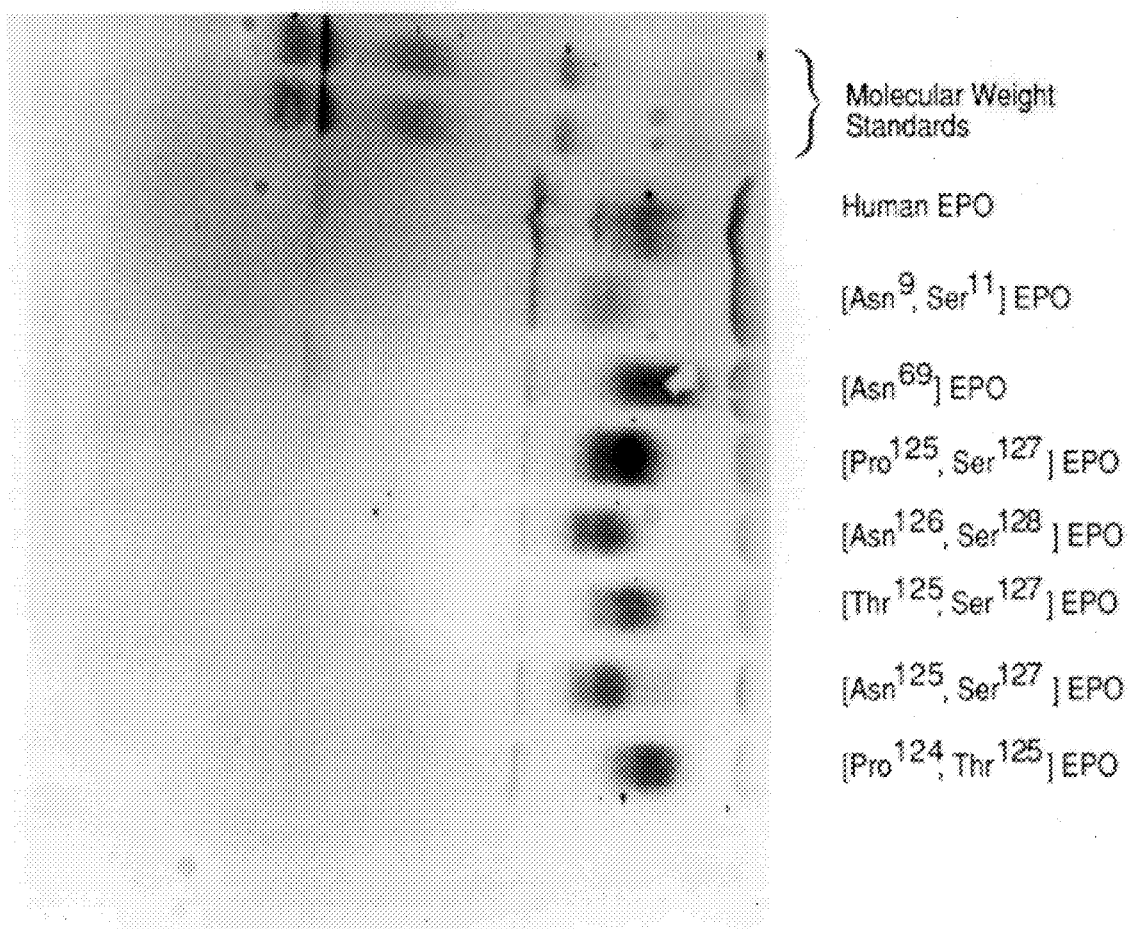
FIG. 7 shows a Western blot analysis of COS cell supernatants of human sequence erythropoietin and indicated erythropoietin analogs. The analogs [$Asn^9$, $Ser^{11}$], EPO, [$Asn^{69}$] EPO, [$Asn^{125}$, $Ser^{127}$] EPO, and [$Pro^{124}$, $Thr^{125}$] EPO are constructed as described in Example 6. The analogs [$Pro^{125}$, $Thr^{127}$] EPO, [$Asn^{126}$, $Ser^{128}$] EPO and [$Thr^{125}$, $Ser^{127}$] EPO which do not contain additional carbohydrate chains are shown for comparison.
Figure 8:
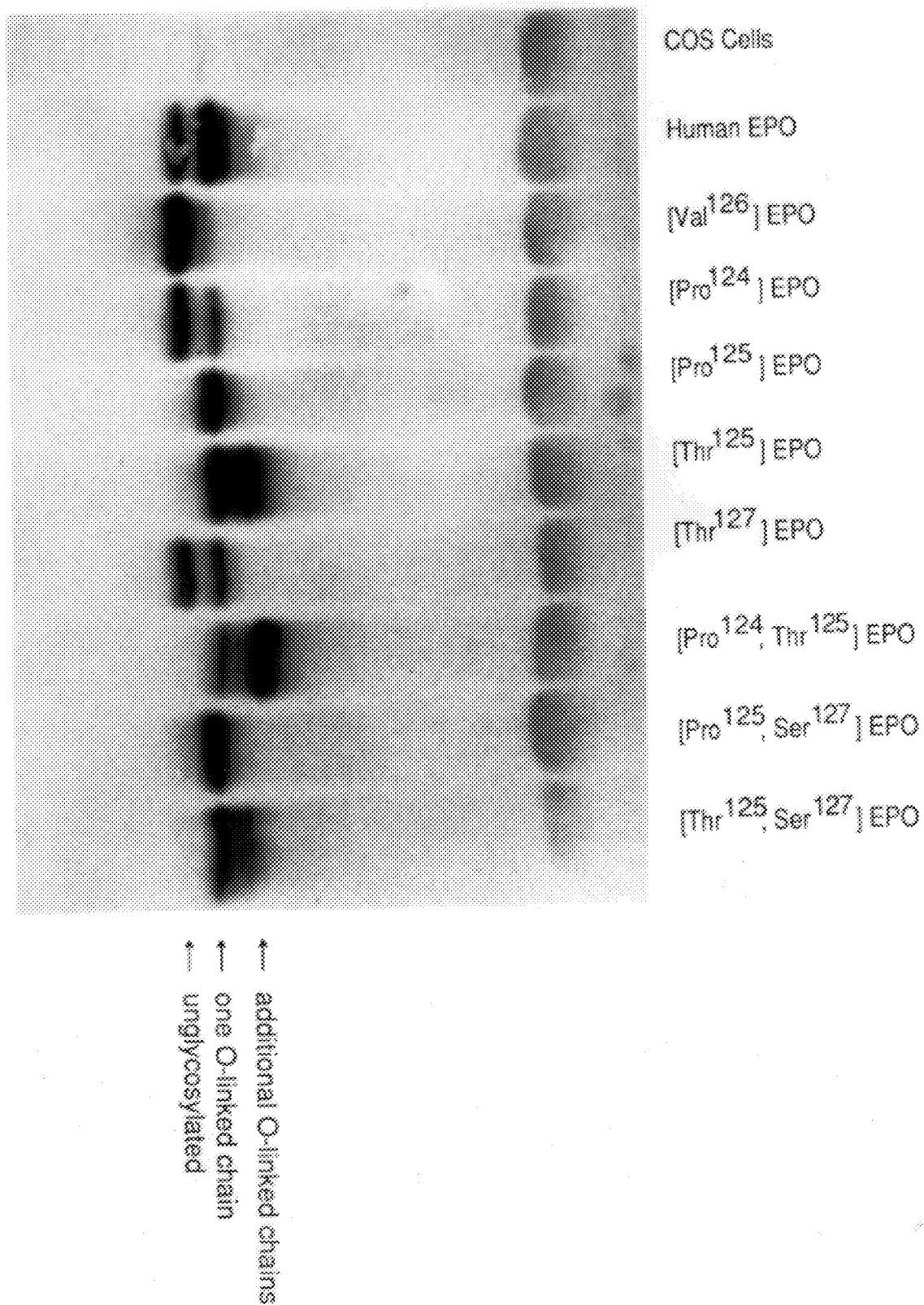
FIG. 8 shows a Western blot analysis of COS cell supernatants of human sequences erythropoietin and indicated erythropoietin analogs after treatment with N-glycanase. The analogs [$Thr^{125}$] EPO and [$Pro^{124}$, $Thr^{125}$] EPO are constructed as described in Example 6. The analogs [$Val^{126}$] EPO, [$Pro^{124}$] EPO, [$Pro^{125}$] EPO, [$Thr^{127}$] EPO, [$Pro^{125}$, $Ser^{127}$] EPO and [$Thr^{125}$, $Ser^{127}$] EPO are shown for comparison.

Analysis of COS cell supernatants transfected with [Asn$^{69}$] EPO and [Asn$^{125}$, Ser$^{127}$] EPO cDNA revealed increased protein size compared to human sequence erythropoietin. This increased size is indicative of an additional N-linked carbohydrate chain (FIG. 7). Treatment of supernatants from COS cells transfected with [Thr$^{125}$] EPO and [Pro$^{124}$, Thr$^{125}$] EPO cDNA with N-glycanase revealed an increased protein size compared to human sequence erythropoietin. This increased size is indicative of an additional O-linked carbohydrate chain (FIG. 8).

D. Isolation of Erythropoietin Analog Isoforms

The erythropoietin analog [Thr$^{125}$] EPO was constructed as described in Section A. An 810 bp. erythropoietin cDNA fragment carrying the [Thr$^{125}$] mutation was isolated by cleaving the plasmid pEC containing the [Thr$^{125}$] mutation with BstEII and BglII and ligating the fragment to pDECΔ, a derivative of pDSα2. pDSα2 is generally described in commonly owned U.S. patent application Ser. No. 501,904, now abandoned, hereby incorporated by reference. pDECΔ was derived from pDSα2 by the following steps:

(1) The HindIII site of pDSα2 was deleted by digesting pDSα2 DNA with HindIII, treating the HindIII cohesive ends with *E. coli* DNA Polymerase (Klenow fragment) and dNTPs, and religating the blunt-ended vector. The resulting plasmid was pDSα2ΔH.

(2) pDSα2ΔH was digested with SalI and a synthetic oligonucleotide having an SV40 splice signal with a SalI linker attached to the 3' end of the splice signal was ligated to it. The synthetic oligonucleotide had the following sequence:

5' TCGAGGAACTGAAAAACCAGAAAGT-
TAACTGGTAAGTTTAGT CTTTTTGTCTTT-

TATTTCAGGTCCCGGATCCGGTGGTGGT-GCAAATCAAGAACTGCTCCTCAGTGGATGTTGC-CTTTACTTCTAGGCCTGTACGG AAGTGT-TACTTCTGCTCTAAAAGCTGCTGCAA-CAAGCTGGTCGACC 3'

The resulting plasmid was pDSα2ΔH splice.

3) pDSα2ΔH splice was digested with SalI and blunt-ended by treating the cohesive ends with T4 DNA polymerase and dNTPs. An 820 bp. BamHI-BglII human erythropoietin CDNA fragment was blunt-ended by the same method and ligated to the plasmid. The resulting plasmid was pDEC.

4) pDEC was digested with KpnI and PvuII and blunt-ended by treating the cohesive ends with mung bean nuclease. The plasmid was religated to delete the excised KpnI-PvuII fragment resulting in the plasmid pDECΔ.

Plasmid pDECΔ containing [Thr$^{125}$] erythropoietin cDNA was transfected into DHFR-deficient CHO cells. 770 ml of CHO cell conditioned medium was concentrated using a 10,000 dalton molecular weight cutoff membrane and diafiltered against 10 mM Tris-HCl, pH 8.6 to a final volume of 34 ml. A 17 ml. aliquot of the concentrate was loaded onto a Q-Sepharose fast flow column (5 ml bed volume) equili-brated in the same buffer and eluted in a linear gradient of 0–250 mM NaCl in 10 mM Tris-HCl, pH 8.6. Aliquots of column fractions, either untreated or digested with N-glycanase, were analyzed by SDS-PAGE or IEF and pools (designated 2, 3 and 4) were made based upon the isoform and/or carbohydrate composition of the fractions. Each pool was loaded onto a Vydac C4 column (214TPB 2030; 1 cm diameter; 1.8–2.5 ml bed volume; 0.34 ml/min) and washed with two column volumes of 20% ethanol in 10 mM Tris-HCl, pH 7.0. The columns were eluted with linear gradients of 20–94% ethanol, 10 mM Tris, pH 7.0. Pools were made, diluted into 10 mM Tris-HCl, pH 7.0, and loaded onto Q-Sepharose fast flow columns. Following a wash in 10 mM Tris-HCl, pH 7.0, the samples were eluted with 20 mM sodium citrate, 250 mM NaCl, pH 7.0. The purified [Thr$^{125}$] pools were analyzed by IEF and are shown in FIG. 9. EPO analog is analyzed for in vivo biological activity as described above (Cotes et al., supra).

While the invention has been described in what is con-sidered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An isolated biologically active erythropoietin isoform having a single isoelectric point and having a specific number of sialic acids per molecule, said number selected from the group consisting of 1–14, and said isoform being the product of the expression of an exogenous DNA sequence in a non-human eucaryotic host cell.

2. An erythropoietin isoform according to claim 1 wherein said isoform comprises erythropoietin having the amino acid sequence of 1-165 or 1-166 human erythropoietin.

3. An erythropoietin isoform according to claim 1 having 14 sialic acids per erythropoietin molecule.

4. An erythropoietin isoform according to claim 1 having 13 sialic acids per erythropoietin molecule.

5. An erythropoietin isoform according to claim 1 having 10 sialic acids per erythropoietin molecule.

6. An erythropoietin isoform according to claim 1 wherein said eucaryotic host cell is a CHO cell.

7. A pharmaceutical composition comprising a therapeu-tically effective amount of said erythropoietin isoform of claim 1 and a pharmaceutically acceptable diluent, adjuvant or carrier.

8. A composition consisting essentially of two or three erythropoietin isoforms according to claim 1.

9. A composition according to claim 8 wherein said isoforms have from 1 to 12 sialic acids per erythropoietin molecule.

10. A composition according to claim 9 wherein said isoforms have 9, 10 and 11 sialic acids per erythropoietin molecule.

11. A composition according to claim 8 wherein said isoforms have greater than 11 sialic acids per erythropoietin molecule.

12. A composition according to claim 11 wherein said isoforms have from 13–14 sialic acids per erythropoietin molecule.

13. Erythropoietin consisting essentially of erythropoietin molecules having a single specific number of sialic acids per molecule, said number selected from the group consisting of 1–14, and said molecules being the product of the expression of an exogenous DNA sequence in a non-human eucaryotic host cell.

14. Erythropoietin according to claim 13 having 14 sialic acids per erythropoietin molecule.

15. Erythropoietin according to claim 13 having 13 sialic acids per erythropoietin molecule.

16. Erythropoietin according to claim 13 having 10 sialic acids per erythropoietin molecule.

17. Erythropoietin according to claim 13 wherein said erythropoietin has the amino acid sequence of human eryth-ropoietin.

18. A pharmaceutical composition comprising a therapeu-tically effective amount of the erythropoietin according to claim 13 and a pharmaceutically acceptable diluent, adju-vant or carrier.

19. A composition consisting essentially of erythropoietin molecules according to claim 13 having two or three specific numbers of sialic acids per erythropoietin molecule.

20. A composition according to claim 19 wherein said molecules have from 1 to 12 sialic acids per erythropoietin molecule.

21. A composition according to claim 19 wherein said molecules have greater than 11 sialic acids per erythropoi-etin molecule.

22. A composition according to claim 21 wherein said molecules have 13 and 14 sialic acids per erythropoietin molecule.

23. A method of preparing an erythropoietin isoform according to claim 1 comprising the steps of:

subjecting a purified erythropoietin to preparative isoelec-tric focusing, and eluting a single isoform.

24. A method of preparing erythropoietin molecules hav-ing a predetermined number of sialic acids per molecule said number selected from the group consisting of 1–14, com-prising applying material containing erythropoietin to an ion exchange column and selectively eluting said molecules from the column.

25. A method of preparing erythropoietin molecules hav-ing a predetermined number of sialic acids per molecule said number selected from the group consisting of 1–14, com-prising applying material containing erythropoietin to a chromatofocusing column and selectively eluting said mol-ecules from the column.

26. A method of increasing hematocrit levels in mammals comprising administering a therapeutically effective amount of the composition according to claim 19.

27. A method for obtaining an erythropoietin composition having a predetermined in vivo specific activity comprising preparing a mixture of two or more erythropoietin isoforms of claim 1.

28. The method of claim 27 wherein said mixture consists essentially of at least two isoforms having less than 12 sialic acids per molecule.

29. The method of claim 28 wherein said mixture consists essentially of erythropoietin isoforms having 9, 10 and 11 sialic acids per molecule.

30. The method of claim 27 wherein said mixture consists essentially of at least two isoforms having greater than 11 sialic acids per molecule.

31. The method as in claim 28 wherein said mixture consists essentially of erythropoietin isoforms having 13 and 14 sialic acids per molecule.

* * * * *

UNITED STATES PATENT AND TRADEMARK OFFICE
CERTIFICATE OF CORRECTION

PATENT NO. : 5,856,298
DATED : January 5, 1999
INVENTOR(S) : Strickland, Thomas

It is certified that error appears in the above-identified patent and that said Letters Patent is hereby corrected as shown below:

Column 13, line 43 change "O" to -- Q --.

Column 14, line 45 change "O" to -- Q --.

Column 17, line 29 change "[Asn4, Ser6]" to -- $[Asn^4, Ser^6]$ --.

Column 17, line 29 change "[Asn9, Ser11]" to -- $[Asn^9, Ser^{11}]$ --.

Signed and Sealed this

Eighteenth Day of May, 1999

*Attest:*

Q. TODD DICKINSON

*Attesting Officer*   Acting Commissioner of Patents and Trademarks